US010052208B2

(12) United States Patent
Fell

(10) Patent No.: US 10,052,208 B2
(45) Date of Patent: Aug. 21, 2018

(54) SURGICALLY IMPLANTABLE KNEE PROSTHESIS WITH CAPTURED KEEL

(71) Applicant: Barry M. Fell, Hummelstown, PA (US)

(72) Inventor: Barry M. Fell, Hummelstown, PA (US)

(*) Notice: Subject to any disclaimer, the term of this patent is extended or adjusted under 35 U.S.C. 154(b) by 0 days.

(21) Appl. No.: 15/240,473

(22) Filed: Aug. 18, 2016

(65) Prior Publication Data

US 2017/0105842 A1  Apr. 20, 2017

Related U.S. Application Data

(63) Continuation of application No. 12/599,123, filed as application No. PCT/US2008/063172 on May 15, 2008, now abandoned.

(60) Provisional application No. 60/938,012, filed on May 15, 2007.

(51) Int. Cl.
*A61F 2/38* (2006.01)
*A61F 2/30* (2006.01)

(52) U.S. Cl.
CPC ............ *A61F 2/389* (2013.01); *A61F 2/3836* (2013.01); *A61F 2/3886* (2013.01); *A61F 2002/30125* (2013.01); *A61F 2002/30884* (2013.01); *A61F 2002/3895* (2013.01)

(58) Field of Classification Search
CPC ................... A61F 2/389; A61F 2/3859; A61F 2002/30125; A61F 2002/30884; A61F 2002/3895; A61F 2002/30841; A61F 2002/30897
See application file for complete search history.

(56) References Cited

U.S. PATENT DOCUMENTS

| 3,869,731 A | 3/1975 | Waugh et al. |
| 3,953,899 A | 5/1976 | Charnley |
| 4,052,753 A | 10/1977 | Dedo |
| 4,207,627 A | 6/1980 | Cloutier |
| 4,344,193 A | 8/1982 | Kenny |
| 4,364,389 A | 12/1982 | Keller |
| 4,385,404 A | 5/1983 | Sully et al. |
| 4,446,578 A | 5/1984 | Perkins et al. |

(Continued)

FOREIGN PATENT DOCUMENTS

| EP | 1136045 A2 | 9/2001 |
| FR | 2700262 A1 | 7/1994 |
| FR | 2738739 A1 | 3/1997 |

OTHER PUBLICATIONS

"U.S. Appl. No. 12/599,123, Advisory Action dated Jul. 17, 2012", 3 pgs.

(Continued)

*Primary Examiner* — Brian Dukert
(74) *Attorney, Agent, or Firm* — Schwegman Lundberg & Woessner, P.A.

(57) ABSTRACT

A unicompartmental knee prosthesis for implantation in a knee joint between a femoral condyle and a corresponding tibia plateau is provided including a generally elliptical body having opposed femoral and tibial face, the body having an anterior end and a posterior end. A keel is provided on the tibial face having a generally anterior-posterior orientation, the keel having an anterior end and a posterior end, where the keel posterior end includes a distal posterior portion that extends farther toward the body posterior end compared with a proximal posterior portion of the keel posterior end.

19 Claims, 39 Drawing Sheets

(56) References Cited

U.S. PATENT DOCUMENTS

| | | |
|---|---|---|
| 4,502,161 A | 3/1985 | Wall |
| 4,722,948 A | 2/1988 | Sanderson |
| 4,759,767 A | 7/1988 | Lacey |
| 4,808,185 A | 2/1989 | Penenberg et al. |
| 4,822,362 A | 4/1989 | Walker et al. |
| 4,880,429 A | 11/1989 | Stone |
| 4,919,667 A | 4/1990 | Richmond |
| 5,007,934 A | 4/1991 | Stone |
| 5,067,964 A | 11/1991 | Richmond et al. |
| 5,074,880 A | 12/1991 | Mansat |
| 5,109,589 A | 5/1992 | Cramer et al. |
| 5,137,536 A | 8/1992 | Koshino |
| 5,158,574 A | 10/1992 | Stone |
| 5,171,322 A | 12/1992 | Kenny |
| 5,263,987 A | 11/1993 | Shah |
| 5,271,737 A | 12/1993 | Baldwin et al. |
| 5,278,201 A | 1/1994 | Dunn et al. |
| 5,344,459 A | 9/1994 | Swartz |
| 5,387,240 A | 2/1995 | Pottenger et al. |
| 5,480,446 A | 1/1996 | Goodfellow et al. |
| 5,496,682 A | 3/1996 | Quadir et al. |
| 5,549,688 A | 8/1996 | Ries et al. |
| 5,683,468 A | 11/1997 | Pappas |
| 5,702,466 A | 12/1997 | Pappas et al. |
| 5,725,584 A | 3/1998 | Walker et al. |
| 5,766,256 A | 6/1998 | Oudard et al. |
| 5,776,200 A | 7/1998 | Johnson et al. |
| 5,795,353 A | 8/1998 | Felt |
| 5,871,541 A | 2/1999 | Gerber |
| 5,888,220 A | 3/1999 | Felt et al. |
| 5,902,599 A | 5/1999 | Anseth et al. |
| 5,957,979 A | 9/1999 | Beckman et al. |
| 5,964,808 A | 10/1999 | Blaha et al. |
| 6,206,927 B1 | 3/2001 | Fell et al. |
| 6,210,444 B1 | 4/2001 | Webster et al. |
| 6,258,127 B1 | 7/2001 | Schmotzer |
| 6,299,645 B1 | 10/2001 | Ogden |
| 6,558,421 B1 | 5/2003 | Fell et al. |
| 6,712,855 B2 | 3/2004 | Martin et al. |
| 6,966,928 B2 | 11/2005 | Fell et al. |
| 7,341,602 B2 | 3/2008 | Fell et al. |
| 2002/0099446 A1 | 7/2002 | Macarthur |
| 2004/0220677 A1 | 11/2004 | Delfosse et al. |
| 2005/0125068 A1 | 6/2005 | Hozack et al. |
| 2006/0235537 A1 | 10/2006 | Kuczynski et al. |
| 2006/0241117 A1* | 10/2006 | Sun ............... C07D 213/81 514/252.03 |
| 2007/0005142 A1 | 1/2007 | Rhodes et al. |
| 2007/0016163 A1 | 1/2007 | Santini et al. |
| 2007/0100462 A1 | 5/2007 | Lang et al. |
| 2007/0299532 A1 | 12/2007 | Rhodes et al. |
| 2010/0249941 A1 | 9/2010 | Fell et al. |

OTHER PUBLICATIONS

"U.S. Appl. No. 12/599,123, Appeal Brief filed Feb. 26, 2014", 13 pgs.
"U.S. Appl. No. 12/599,123, Appeal Decision mailed Jun. 21, 2016", 8 pgs.
"U.S. Appl. No. 12/599,123, Decision on Pre-Appeal Brief Request mailed Dec. 26, 2013", 2 pgs.
"U.S. Appl. No. 12/599,123, Examiner's Answer to Appeal Brief dated May 7, 2014", 6 pgs.
"U.S. Appl. No. 12/599,123, Final Office Action dated Apr. 12, 2012", 12 pgs.
"U.S. Appl. No. 12/599,123, Final Office Action dated Jun. 18, 2013", 11 pgs.
"U.S. Appl. No. 12/599,123, Non Final Office Action dated Sep. 16, 2011", 10 pgs.
"U.S. Appl. No. 12/599,123, Non Final Office Action dated Oct. 2, 2012", 10 pgs.
"U.S. Appl. No. 12/599,123, Pre-Appeal Brief Request filed Nov. 18, 2013", 4 pgs.
"U.S. Appl. No. 12/599,123, Preliminary Amendment filed Nov. 6, 2009", 4 pgs.
"U.S. Appl. No. 12/599,123, Reply Brief filed Jul. 7, 2014", 4 pgs.
"U.S. Appl. No. 12/599,123, Response filed Jan. 17, 2012 to Non Final Office Action dated Sep. 16, 2011", 8 pgs.
"U.S. Appl. No. 12/599,123, Response filed Mar. 4, 2013 to Non Final Office Action dated Oct. 2, 2012", 9 pgs.
"U.S. Appl. No. 12/599,123, Response filed Jul. 2, 2012 to Final Office Action dated Apr. 12, 2012", 10 pgs.
"U.S. Appl. No. 12/599,123, Response filed Aug. 30, 2011 to Restriction Requirement dated Aug. 17, 2011", 10 pg.
"U.S. Appl. No. 12/599,123, Restriction Requirement dated Aug. 17, 2011", 6 pgs.
"Australian Application Serial No. 2008255048, Office Action dated Feb. 4, 2014", 3 pgs.
"Australian Application Serial No. 2008255048, Office Action dated Sep. 17, 2012", 3 pgs.
"Australian Application Serial No. 2008255048, Response filed Nov. 29, 2013 to Office Action dated Sep. 17, 2012", 21 pgs.
"Canadian Application Serial No. 2,684,759, Office Action dated Apr. 16, 2014", 3 pgs.
"Canadian Application Serial No. 2,684,759, Office Action dated Nov. 27, 2014", 3 pgs.
"Canadian Application Serial No. 2,684,759, Response filed Feb. 3, 2015 to Office Action dated Nov. 27, 2014", 7 pgs.
"Canadian Application Serial No. 2,684,759, Response filed Oct. 8, 2014 to Office Action dated Apr. 16, 2014", 10 pgs.
"European Application Serial No. 08755543.9, Communication Pursuant to Article 94(3) EPC dated Aug. 11, 2014", 5 pgs.
"European Application Serial No. 08755543.9, Decision to grant dated Aug. 20, 2015", 3 pgs.
"European Application Serial No. 08755543.9, Extended European Search Report dated Apr. 17, 2013", 6 pgs.
"European Application Serial No. 08755543.9, Intention to grant dated Apr. 22, 2015", 6 pgs.
"European Application Serial No. 08755543.9, Response filed Jan. 21, 2015 to Communication Pursuant to Article 94(3) EPC dated Aug. 11, 2014", 34 pgs.
"European Application Serial No. 08755543.9, Response filed Mar. 3, 2014 to Extended European Search Report dated Apr. 17, 2013", 11 pgs.
"International Application Serial No. PCT/US2008/063712, International Preliminary Report on Patentability dated Nov. 17, 2009", 7 pgs.
"International Application Serial No. PCT/US2008/063712, International Search Report dated Sep. 26, 2008", 1 pg.
"International Application Serial No. PCT/US2008/063712, Written Opinion dated Sep. 26, 2008", 6 pgs.

\* cited by examiner

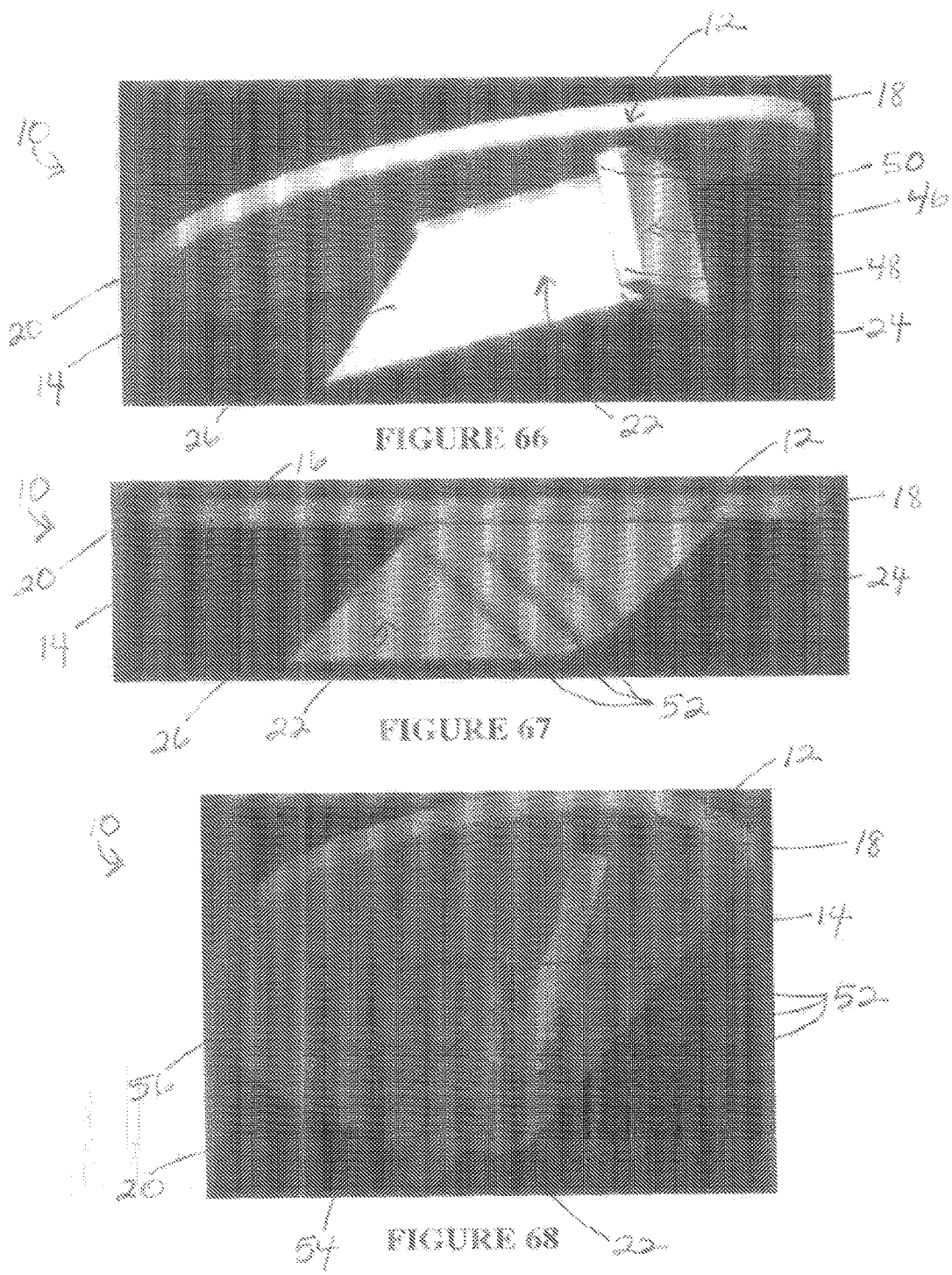

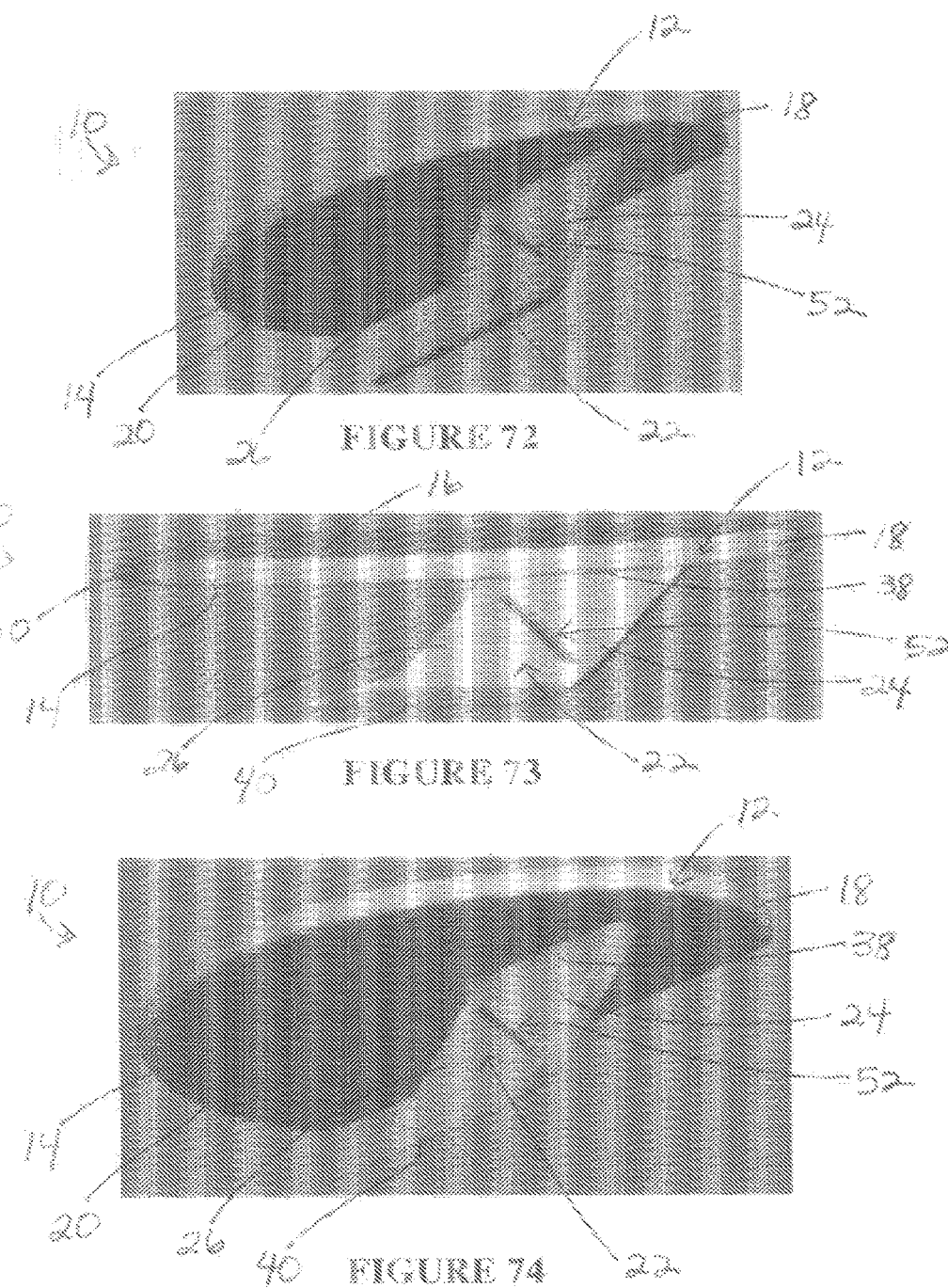

SURGICALLY IMPLANTABLE KNEE PROSTHESIS WITH CAPTURED KEEL

CROSS-REFERENCE TO RELATED APPLICATIONS

This application is a continuation of U.S. patent application Ser. No. 12/599,123 filed Nov. 6, 2009, which claims the benefit of U.S. provisional application Ser. No. 60/938,012 filed May 15, 2007, which is incorporated by reference herein.

BACKGROUND OF THE INVENTION

1. Field of the Invention

This invention relates to a prosthesis which is surgically implantable into a body joint, such as the knee.

2. Background Art

Current knee arthroplasties typically involve replacement of the arthritic joint surfaces and are known for their use of metal and plastic components. They are usually embedded in a polymethylmethacrylate (PMMA) cement mantle to adhesively and mechanically bond the components to the area of bone exposed during the course of surgery.

Typically, this area of exposed bone is 2-3 mm below the area of existing eroded bone surface and generally requires removal of the entire subchondral bone in the area of implant location. In all cases, the subchondral (SC) bone of the tibial plateau, which is attached to the remaining articular surface, is removed as standard practice for both the total knee (TKR) and partial or unicompartmental knee (UKR) replacement procedures.

Further, FDA guidelines generally dictate that when polyethylene (PE) is used as a bearing surface, whether in conjunction with a metal support plate or not, at least 6 mm of PE thickness must be used to prevent fracturing of the PE during use. When the PE is used on the tibial side of these implant designs, this requirement leads to bone resections of the tibial plateau generally greater than 7 mm. The subchondral bone thickness on a typical tibial plateau is generally 2-3 mm. Thus, a typical TKR or UKR implant will require resection of the entire SC bone present on the tibial plateau, leaving only cancellous bone.

The PE is typically held in place by an interference fit or by melt infusion to a metal backing plate known as the tibial baseplate. This baseplate, in turn, is held in place on the now exposed cancellous bone of the tibia by screws, keels, posts, or combinations of some or all of these devices. The screws and keels generally provide immediate fixation, but these are usually enhanced by the addition of the PMMA cement. In the case of perforated keels, tapered and hourglass shaped posts, when these projections are set in uncured cement, the cement forms around and through them and, once hardened, provides an almost indestructible bond between the PMMA cement and the tibial baseplate. The cement also permeates the open cellular structure of the cancellous bone, thus resulting in the same type of bond between the bone and the tibial baseplate. In some unique cases, the metal tibial baseplate is not used and an all-PE design is bonded directly to the cancellous bone with the PMMA cement utilizing a roughened PE surface or molded posts to facilitate the bond with the PMMA cement.

A new generation of tibial hemiarthroplasty (THA) implant designs has been introduced which do not require significant resection of the SC bone of the tibial plateau to function properly. Examples of this are the U.S. Pat. Nos. 6,206,927; 6,558,421; 6,966,928; 6,866,684; and 7,341,602, each of which is incorporated by reference herein. These THA designs maintain their proper location in the joint by interference with preexisting or prepared anatomical shapes present in the knee joint, and none require PMMA-cemented protrusions or screws for proper function.

Previous keel designs, whether utilized for THA, UKR, or TKR implants, typically utilize an anteriorly-oriented keel. For example, the Zimmer Sbarbaro "skate" implant has a keel aligned in the anterior-posterior (AP) direction, with the posterior portion being rounded and sharpened and the anterior portion having an anterior (forward) pointing distal tip. In order to insert this particular shaped keel into a tibia with a cut to accept the keel, the length of the saw cut needed to insert the bottommost portion of the keel would be significantly longer the length of the keel at the base of the implant, thus allowing the implant to be able to slide in an anterior fashion upon implantation in an anterior to posterior insertion direction.

Other previous keel designs, such as the DePuy "Preservation" UKR, utilize a keel which extends the majority of the length of the baseplate. In this implant, the keel also comprises an hourglass shape in medial-lateral (ML) section. Due to the length of the keel and the hourglass design along its length, this implant cannot be inserted into the tibia without first making a substantial femoral cut to provide access to the tibia, or otherwise inserting the implant via a lengthwise insertion from the most anterior portion of the tibial plateau. In other words, the tibial plateau, rather than receiving a simple angle saw cut in order to receive the implant, must have a milled hourglass shape cut in the plateau which extends through the most anterior cortical bone in order for the keel to be inserted into the joint. If such a milled cut is not prepared, then a cut equal to the largest width of the keel must be made, which would not provide positive locking with the keel unless a mantle of cement is used.

BRIEF DESCRIPTION OF THE DRAWINGS

FIG. 66 is a bottom perspective view of the prosthesis of FIG. 65;

FIG. 67 is a side elevational view of a prosthesis according to the present invention including a keel with an angled posterior end, a rounded, angled anterior end, and a plurality of angled barb members oriented toward the anterior end;

FIG. 68 is a bottom perspective view of the prosthesis of FIG. 67;

FIG. 72 is a bottom perspective view of the prosthesis of FIG. 71;

FIG. 73 is a side elevational view of a prosthesis according to the present invention including a keel with a hooked posterior end, a rounded, angled anterior end, and an angled barb member oriented toward the anterior end, wherein the keel tapers at a distal end thereof;

FIG. 74 is a bottom perspective view of the prosthesis of FIG. 73;

DETAILED DESCRIPTION OF THE INVENTION

Figure 1:
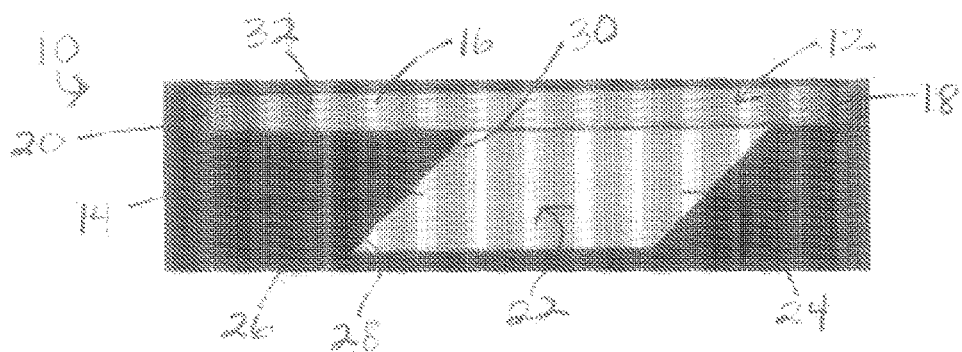
FIG. 1 is a side elevational view of a prosthesis according to the present invention including a keel with angled anterior and posterior ends.

As required, detailed embodiments of the present invention are disclosed herein; however, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

The present invention includes a prosthesis with a captured keel design which provides for positive interlocking that resists unintended dislodgement of the implant without the need for PMMA cement. The prosthesis according to the present invention may be used in conjunction with a tibial preparation that removes much of the remaining cartilage but leaves the majority of the SC bone of the tibial plateau intact. In accordance with the present invention, and differentiated from prior keel designs, the keel disclosed herein incorporates a notched, angled, or other design wherein the most distal, posterior portion of the keel may extend more posteriorly than the most proximal, posterior portion of the keel, thus providing a keel shape of negative draft. In addition, the distal end of the keel may be longer in an AP direction than the proximal end of the keel, giving a recessed or hooked appearance. The keel may be of sufficient depth such that while the bottom of the prosthesis sits predominantly on the existing SC bone, the extended portion of the keel may reach below the underside of the SC bone, thus capturing the prosthesis with the remaining SC bone.

By leaving the majority of the SC bone intact and undisturbed in accordance with the present invention, the risk over time of prosthesis subsidence into the tibia, the primary failure mode of present day UKR implants, may be largely eliminated. This may be of great significance to patients who have unicompartmental disease but are contra-indicated for UKR or TKR procedures because of gross obesity. Further, unlike other THA implants, the captured keel prosthesis according to the present invention may provide for significantly reduced motion against the tibia because of the interlocking keel design.

One function of the prosthesis according to the present invention may be to effectively replace the articular material that has been lost due to the effects of osteoarthritis by spanning the diseased area and supporting the prosthesis by intimate contact with the surrounding healthy tissue. An advantage of this approach is that the combination of removing healthy articular material and replacing that same material with the prosthesis allows for a minimal thickness prosthesis to be utilized which does not need to disturb the meniscal function or location. This approach may result in an area under the prosthesis where the prosthesis is barely in contact with the area of osteoarthritis (where SC bone has been deformed or eburnated). The prosthesis according to the present invention may not disturb SC bone, thus reducing the chance of any prosthesis subsidence into cancellous bone like a UKR baseplate often does.

In accordance with the present invention, unlike previous THA and UKR methods, it is not necessary that the tibial plateau have an absolutely flat surface after surgical preparation. Rather, the majority of the plateau, once the remaining articular material has been largely removed, may provide an adequate peripheral shoulder on which the prosthesis can be supported. Thus, if the area of the osteoarthritis defect were still lower than the SC bone once the majority of the plateau has been flattened, the prosthesis may simply bridge this area while the keel may pass through the defect to the underside of the SC bone in that area, providing an interlocking behavior.

The keel of the prosthesis according to the present invention is arranged to be at least partially received within a cut prepared on the tibial plateau. According to one aspect of the present invention, the tibial cut may be of a size substantially equal to the size of a proximal end of the keel right underneath the prosthesis, such that little or no give exists between the tibial cut and keel, such that use of cement may be avoided. The desired location and size of the tibial cut may be matched with a particular prosthesis selected from a library of prostheses having different locations and sizes of keels. The tibial cut may be prepared with an appropriate milling device or the like which may be accurately located via temporary fixation, computer guidance, or other means.

The surgical procedure may involve resection (flattening) of the remaining articular material on the tibial plateau in the area where the prosthesis will reside using an oscillating saw or other tool, sizing the plateau for the proper length, width and thickness and, utilizing a cutting guide, making a saw or rasp cut at the proper angle and direction with the oscillating saw. This vertical saw cut may ultimately determine the final position of the prosthesis. The keel of the prosthesis may be positioned into the guided saw cut location with the knee flexed and once in position, gently hammered into place. In addition to not requiring the removal of SC bone, the prosthesis according to the present invention does not require femoral resection to implant.

While the prosthesis according to the present invention is shown and described herein as being implanted in a knee joint, specifically as a unicompartmental knee prosthesis implantable in a knee joint between a femoral condyle and a corresponding tibial plateau, it is understood that the prosthesis could be utilized in joints other than the knee such as, but not limited to, the hip, shoulder, wrist, ankle, or elbow, or other small joints of the foot or hand.

With reference to the figures, the prosthesis according to the present invention, designated generally by reference numeral 10, comprises a body 12 which may be generally elliptical and which includes a bottom, or tibial, face 14 and an opposed top, or femoral, face 16. Body 12 includes an anterior end 18 and a posterior end 20, corresponding to the anatomical location of these ends 18, 20 of body 12 upon implantation into the knee joint, wherein the prosthesis shape may generally cover the majority of the medial or lateral tibial plateau T. To restrain movement of the prosthesis, a keel 22 may be provided on the bottom face 14, and may have a generally AP orientation as depicted herein. According to the present invention, the keel 22 can have any location on the bottom face 14 and can be of any size suitable for insertion. Keel 22 has an anterior end 24 and a posterior end 26, again according to the anatomical location of these ends 24, 26 upon implantation. Keel posterior end 26 may include a distal posterior portion 28 that extends farther toward the body posterior end 20 compared with a proximal posterior portion 30 of the keel posterior end 26, creating a posterior keel design which is relieved, undercut, hooked, or similar. The keel designs according to the present invention provide inherent stability to the prosthesis 10 because femoral loading on the prosthesis 10 cannot reproduce motion of the prosthesis 10 required to dislodge it from the tibial plateau T. In addition to the embodiments depicted herein, it is understood that any keel having a distal posterior portion extending further toward the body posterior end than does the proximal posterior portion of the keel is fully contemplated according to the present invention.

The top face 16 could be of uniform shape or could have a combination of sloped and flat surfaces. The entire top face 16 or portions thereof may range from generally convex to generally concave or combinations of those surfaces, and range from generally conformal to non-conformal, depending on the compartment for implantation, the condition of the ligaments and other soft tissue structure at the time of surgery, and how much stability the knee will require. The femoral face 16 shape may be characterized as an aspect ratio defined by the chord line and the thickness above or below this chord line as a function of distance from a defined point on the chord line, such as the leading edge or midpoint, much like an airfoil can be described. It is understood that the terms "concave" and "convex" as used herein are not restricted to describing surfaces with a constant radius of curvature, but rather are used to denote the general appearance of the surface.

According to one aspect of the present invention, the remainder of the bottom face 14, excluding the keel 22, may include, for example, a generally flat surface which does not require "seating." However it is understood that other contours of the bottom face 14 are fully contemplated in accordance with the present invention. For example, depending upon the compartment of implantation, the condition of the ligaments and other soft tissue structure at the time of surgery, and how much stability the knee will require, the bottom face 14 may be generally concave, flat, or convex, or anywhere within the range from concave to convex or combinations of those surfaces. Again, it is understood that the terms "concave" and "convex" as used herein is not restricted to describing a surface with a constant radius of curvature, but rather is used to denote the general appearance of the surface.

The body 12 further includes a peripheral edge 32 extending between the bottom face 14 and the top face 16. Edges along the periphery of the prosthesis 10 can be rounded. Any thickness of the prosthesis 10 or variation of thickness within the prosthesis 10 may be utilized, and may be determined so as to provide proper joint tensioning throughout the range of motion of the knee. The prosthesis 10 according to the present invention may have length and width proportions roughly similar to any of the current UKR tibial base plates, whereas its thickness may generally be 2-3 mm less than the UKR overall baseplate/PE thickness since the SC bone is not being removed. Of course, prosthesis 10 is not limited to these dimensions. The prosthesis 10 according to the present invention may be used in conjunction with the remaining meniscus or meniscal replacement by having a relieved thickness along the periphery where the meniscus is located. Additionally, the posterior end 20 of the femoral face 16 may be tapered, and two different femoral and tibial surface profiles utilized. Thinning of the posterior end 20 may be helpful in deep flexion to eliminate a lever which could tip the prosthesis 10 upward and potentially out of engagement with the tibial plateau T, and also to relieve possible impingement and pain.

It is understood that the term "generally elliptical" is intended to include all construction methods which yield a generally planar shape which is longer in one direction than in the transverse direction and has generally rounded corners, and that the prosthesis 10 is not otherwise limited to any particular shape.

Figure 2:
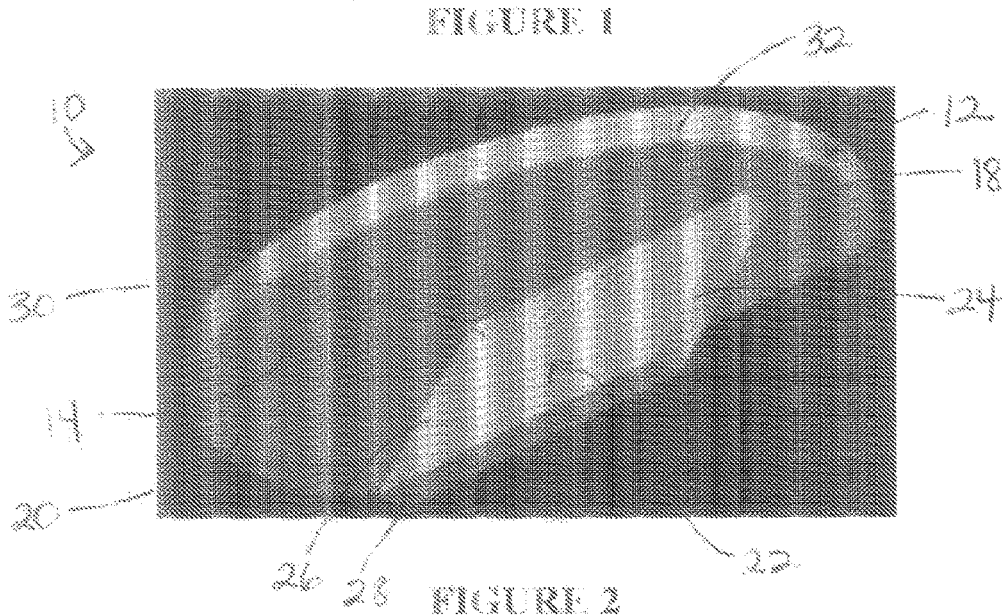
FIG. 2 is a bottom perspective view of the prosthesis of FIG. 1.
Figure 3:
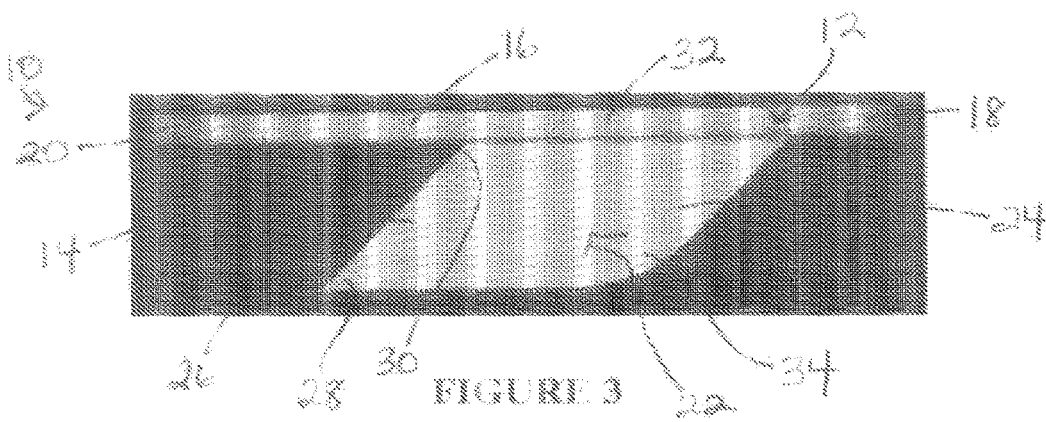
FIG. 3 is a side elevational view of a prosthesis according to the present invention including a keel with a rounded anterior end and angled posterior end.
Figure 4:
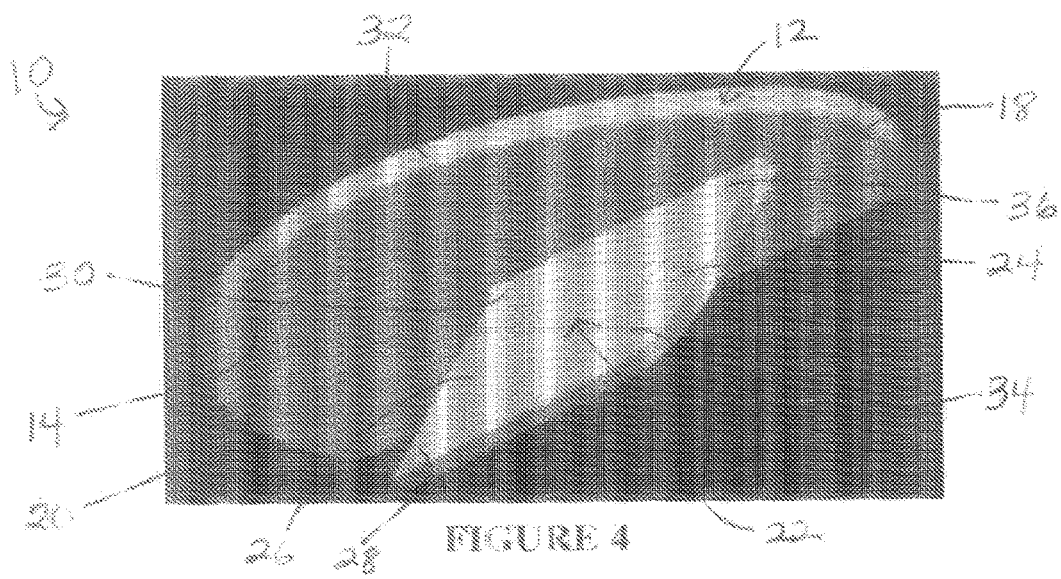
FIG. 4 is a bottom perspective view of the prosthesis of FIG. 3.
Figure 5:
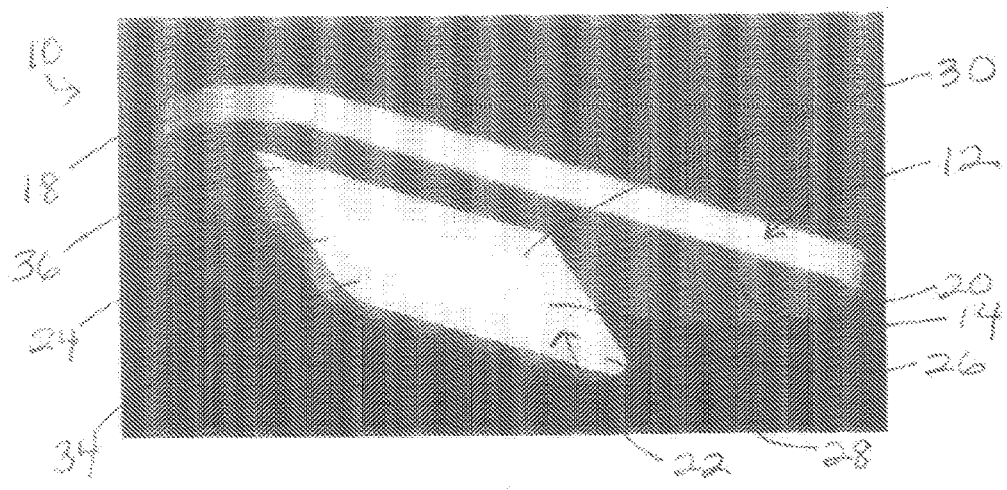
FIG. 5 is a bottom perspective view of a prosthesis according to the present invention including a keel with rounded anterior and posterior ends.
Figure 6:
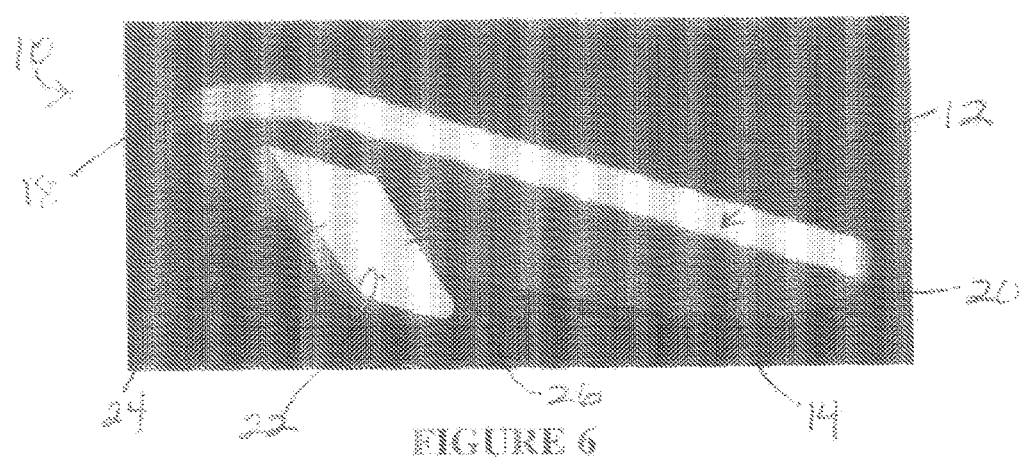
FIG. 6 is a bottom perspective view of a prosthesis according to the present invention including a keel with rounded anterior and posterior ends.
Figure 7:
FIG. 7 is a side elevational view of a prosthesis according to the present invention including a keel with rounded anterior and posterior ends shown with reference to a cross-section of the tibia, wherein a representative thickness subchondral and cortical bone are represented.

With reference first to FIGS. 1-2, a prosthesis 10 according to the present invention is depicted including a keel 22 with anterior and posterior ends 24, 26 which are angled toward the body posterior end 20 such that the distal posterior portion 28 of the keel 22 extends farther toward the body posterior end 20 compared with the proximal posterior portion 30 of the keel 22. This creates an undercut portion at the keel posterior end 26 which may then engage underneath the SC bone upon insertion of the prosthesis 10. Insertion of the prosthesis 10 may be facilitated by rounding of a distal anterior portion 34 of the keel as shown in FIG. 3-4, or rounding of both the distal anterior 34 and distal posterior portions 28 of the keel 22 as depicted in FIGS. 5-7. Alternatively, solely the distal posterior portion 28 of the keel may be rounded.

As shown in FIGS. 5-6, keel 22 may be embodied as having different lengths along tibial face 14 and be positioned differently on tibial face 14. For example, FIG. 5 depicts a keel 22 having a length that extends along approximately half the length of the tibial face 14, positioned toward body anterior end 18, whereas FIG. 6 depicts a keel 22 having a length that extends along approximately 20% of the length of the tibial face 14. Of course, it is understood that any length, depth, and positioning of keel 22 with respect to tibial face 14 is fully contemplated.

Figure 8:
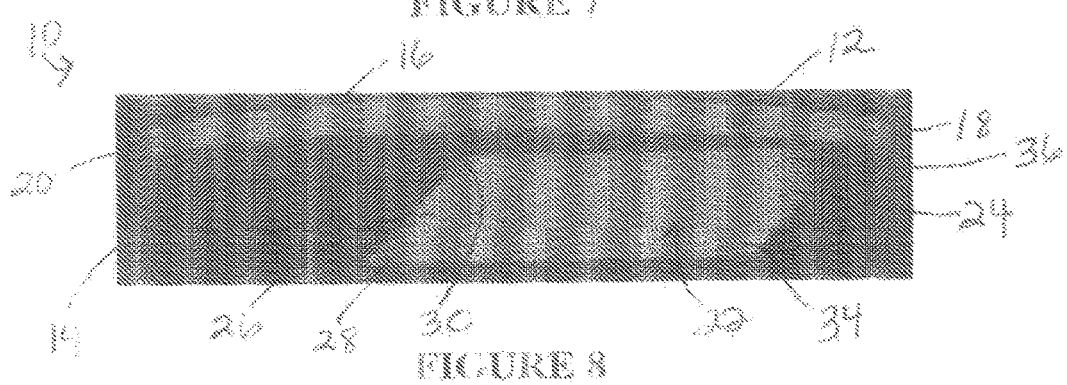
FIG. 8 is a side elevational view of a prosthesis according to the present invention including a keel with an angled posterior end and chamfered anterior end.
Figure 9:
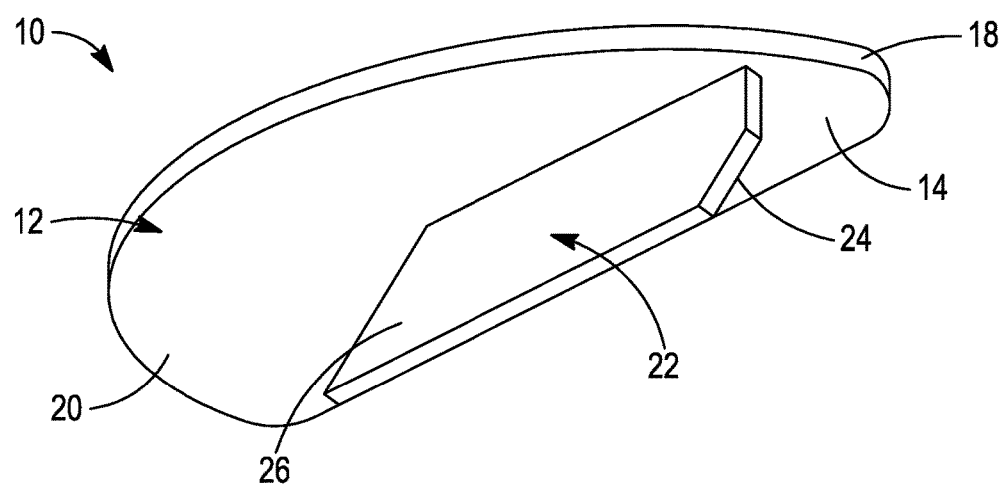
FIG. 9 is a bottom perspective view of the prosthesis of FIG. 8.
Figure 10:
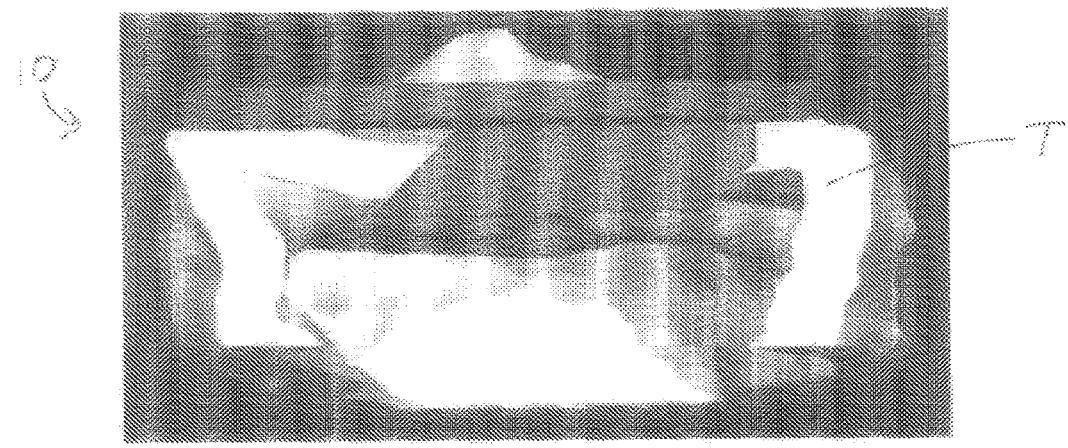
FIG. 10 is a side elevational view of the prosthesis of FIG. 8 shown with reference to a cross-section of a tibia, wherein a representative thickness subchondral and cortical bone are represented.
Figure 11:
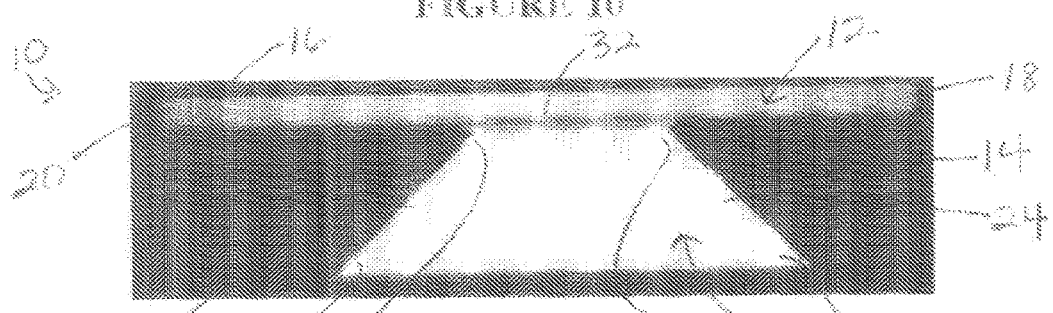
FIG. 11 is a side elevational view of a prosthesis according to the present invention including a keel with an angled posterior end and oppositely angled anterior end.
Figure 12:
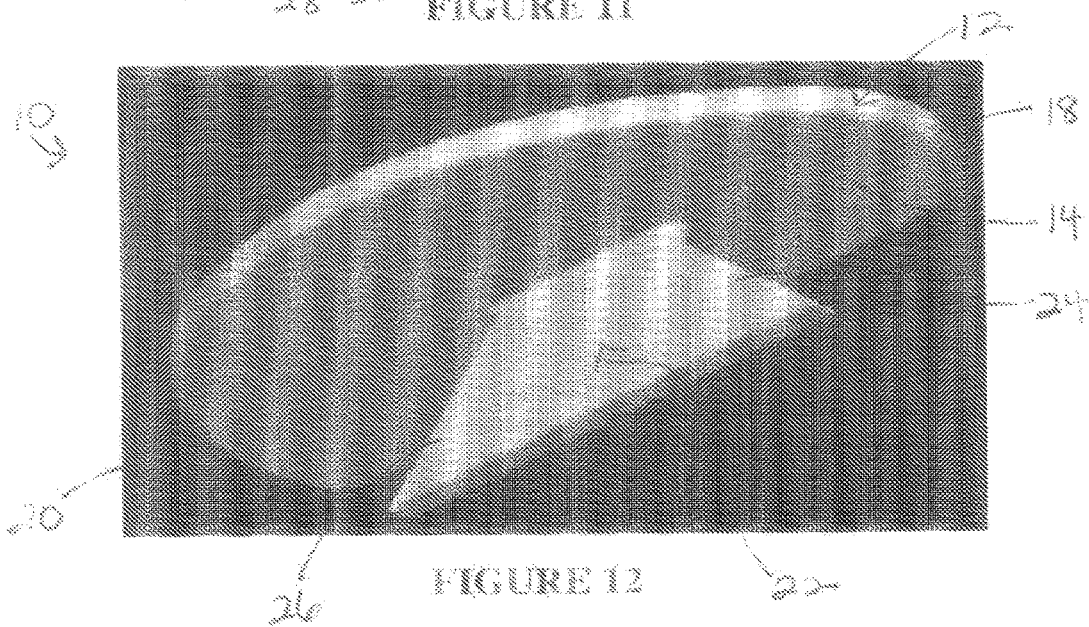
FIG. 12 is a bottom perspective view of the prosthesis of FIG. 11.
Figure 13:
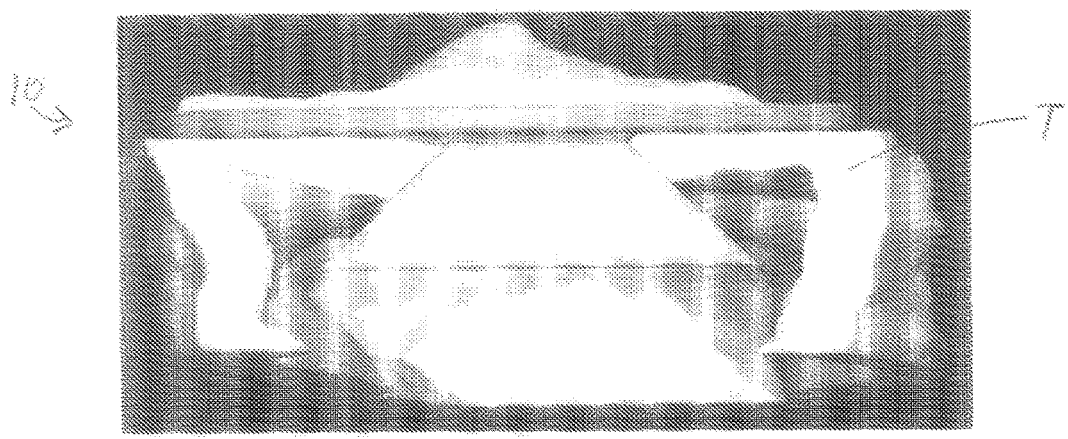
FIG. 13 is a side elevational view of the prosthesis of FIG. 11 shown with reference to a cross-section of a tibia, wherein a representative thickness subchondral and cortical bone are represented.
Figure 14:
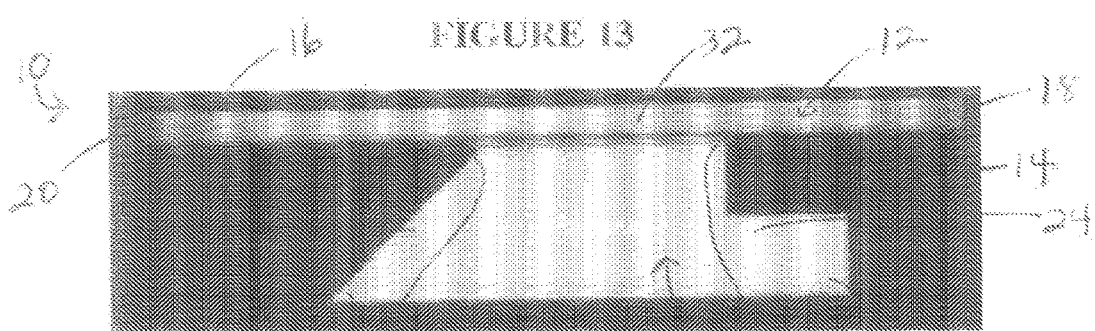
FIG. 14 is a side elevational view of a prosthesis according to the present invention including a keel with an angled posterior end and a step-shaped anterior end.
Figure 15:
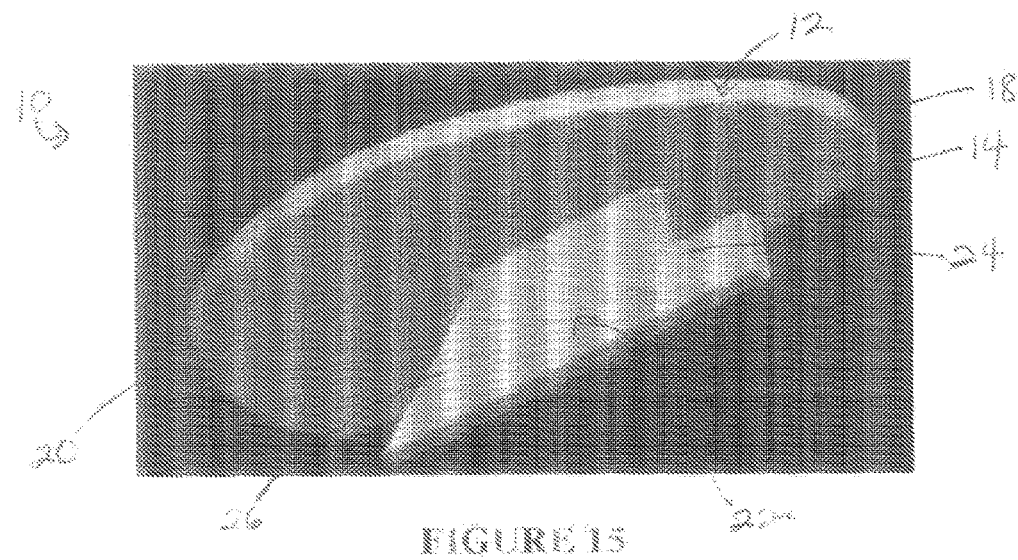
FIG. 15 is a bottom perspective view of the prosthesis of FIG. 14.
Figure 16:
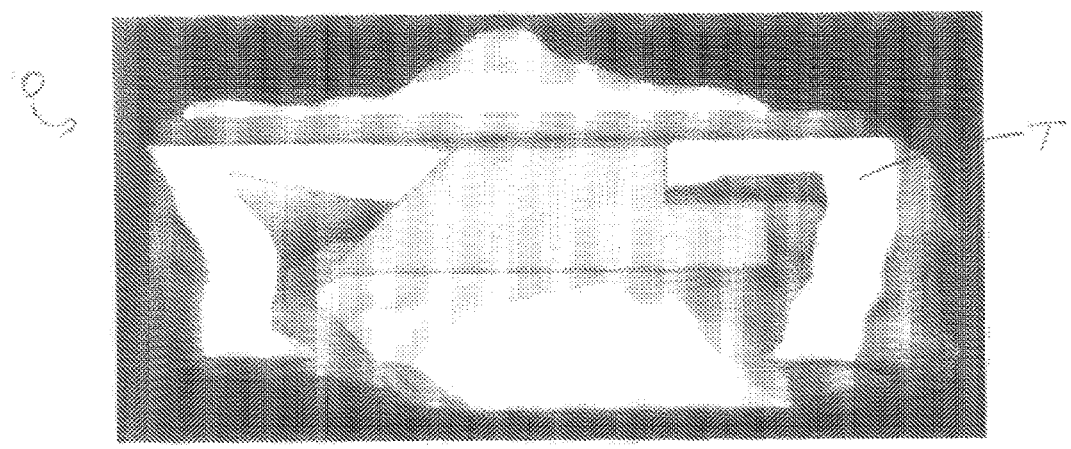
FIG. 16 is a side elevational view of the prosthesis of FIG. 14 shown with reference to a cross-section of a tibia, wherein a representative thickness subchondral and cortical bone are represented.
Figure 17:
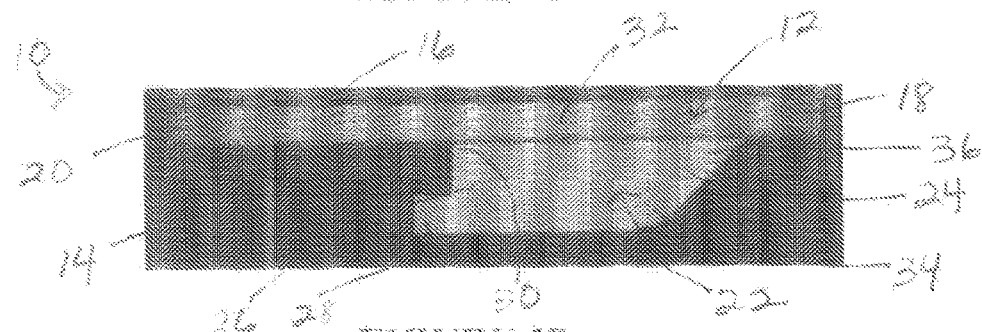
FIG. 17 is a side elevational view of a prosthesis according to the present invention including a keel with a step-shaped posterior end and a rounded anterior end.
Figure 18:
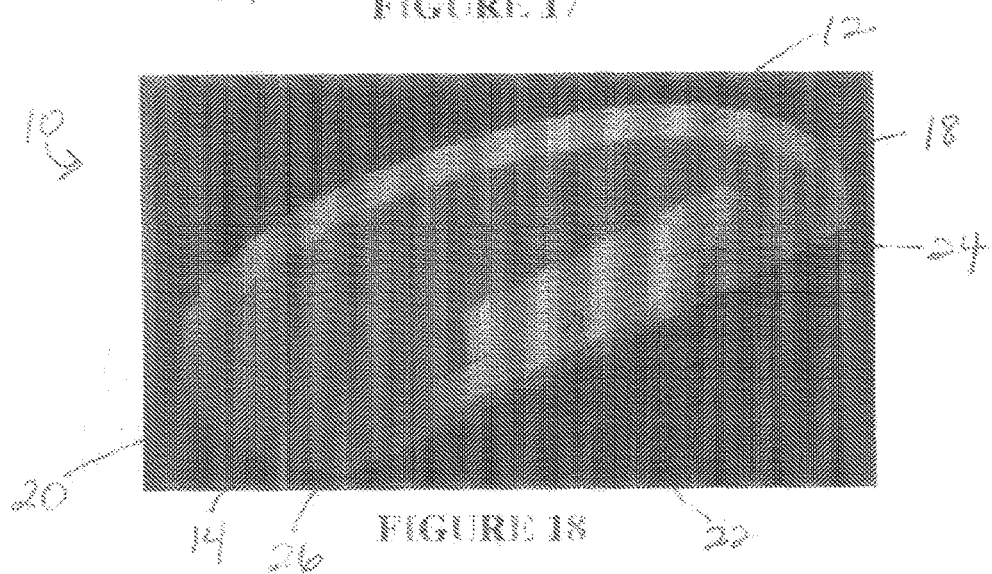
FIG. 18 is a bottom perspective view of the prosthesis of FIG. 17.
Figure 19:
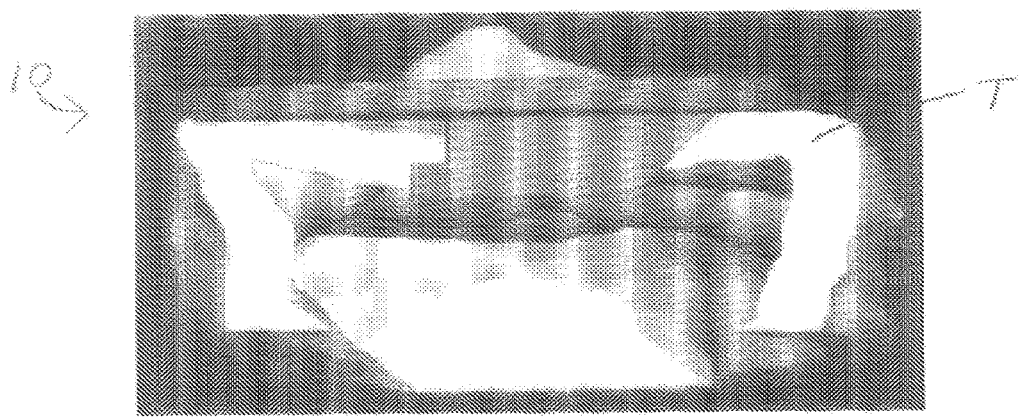
FIG. 19 is a side elevational view of the prosthesis of FIG. 17 shown with reference to a cross-section of a tibia wherein a representative thickness subchondral and cortical bone are represented.
Figure 20:
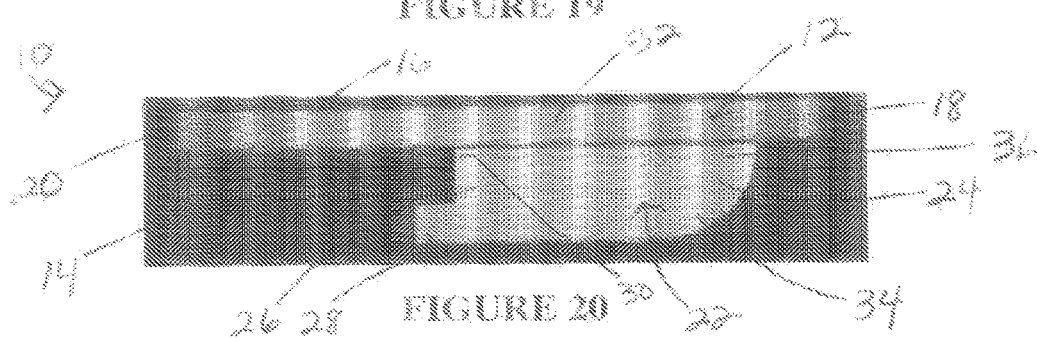
FIG. 20 is a side elevational view of a prosthesis according to the present invention including a keel with a step-shaped posterior end and a curved anterior end.
Figure 21:
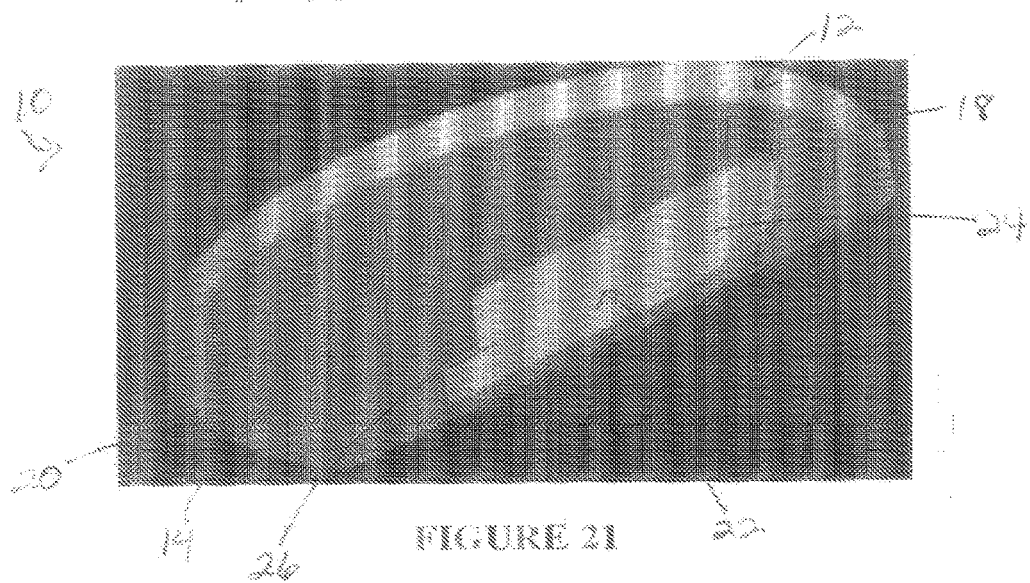
FIG. 21 is a bottom perspective view of the prosthesis of FIG. 20.
Figure 22:
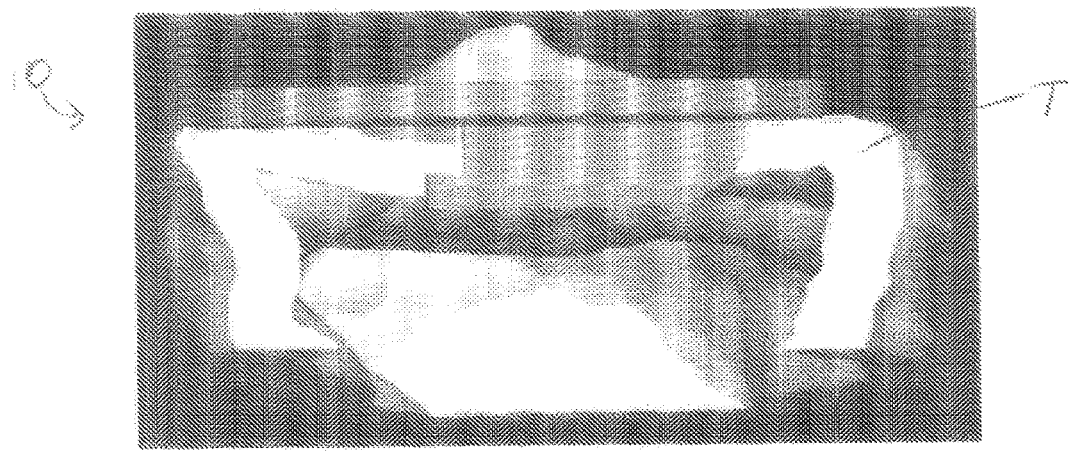
FIG. 22 is a side elevational view of the prosthesis of FIG. 20 shown with reference to a cross-section of a tibia, wherein a representative thickness subchondral and cortical bone are represented.
Figure 23:
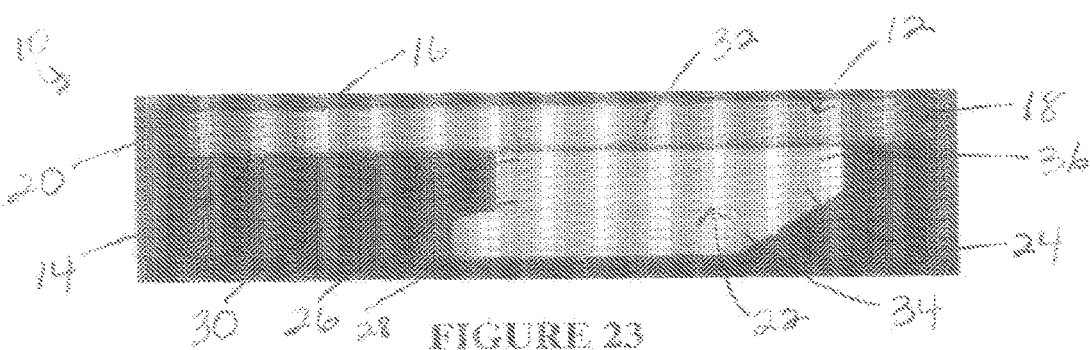
FIG. 23 is a side elevational view of a prosthesis according to the present invention including a keel with a step-shaped posterior end and a chamfered anterior end.
Figure 24:
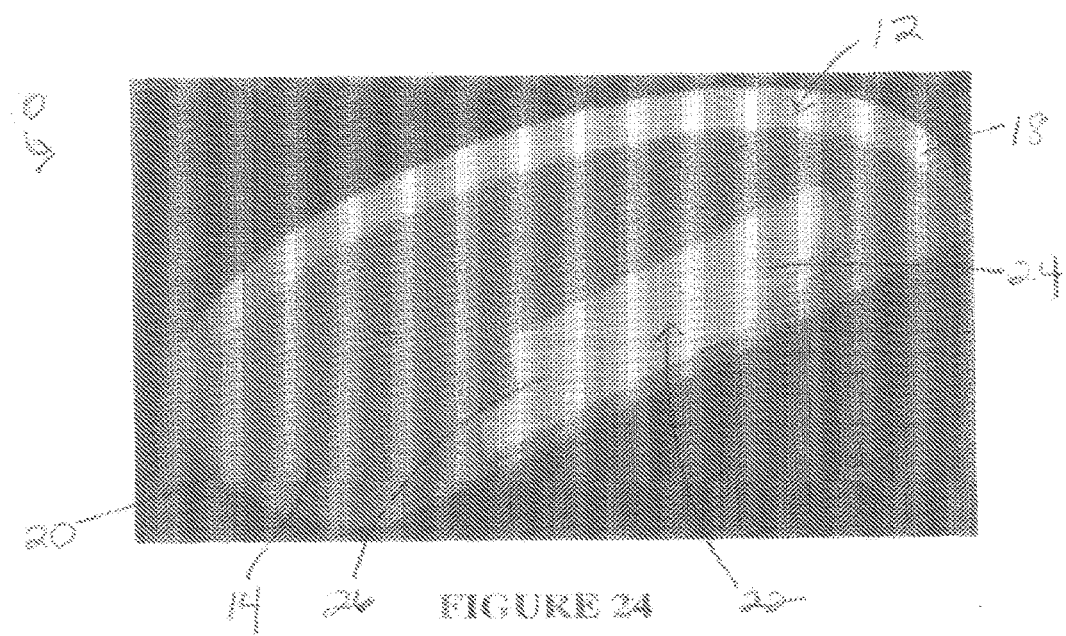
FIG. 24 is a bottom perspective view of the prosthesis of FIG. 23.
Figure 25:
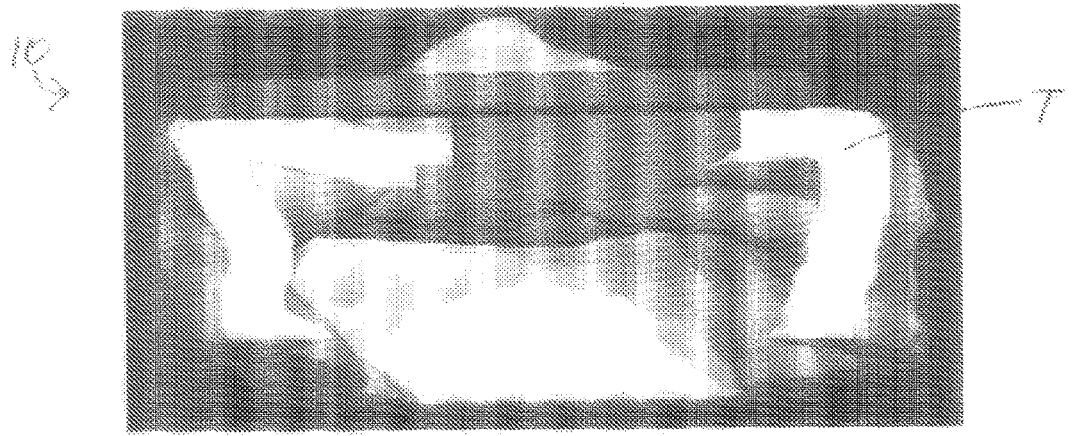
FIG. 25 is a side elevational view or the prosthesis of FIG. 23 shown with reference to a cross-section of a tibia, wherein a representative thickness subchondral and cortical bone are represented.

In accordance with another embodiment of the present invention, FIGS. 8-10 depict a prosthesis including a keel with an angled posterior end 26 and chamfered distal anterior portion 34. FIGS. 17-25 illustrate keel embodiments according to the present invention wherein the keel posterior end 26 includes a notched or step-shaped configuration, such as to form an approximately 90° angle at the keel posterior end 26, and the keel anterior end 24 is angled, rounded, chamfered, or a combination thereof.

With reference to FIGS. 11-16, in addition to the angled posterior end 26 described above, the keel 22 according to the present invention could also incorporate an oppositely angled, notched, or step-shaped anterior end 24 wherein the keel anterior end 24 includes a proximal anterior portion 36 that extends farther toward the body anterior end 18 compared with a distal anterior portion 34 of the keel anterior end 24. Thus, once engaged with the underside of the SC bone, the prosthesis 10 may be secured both anteriorly and posteriorly to preventing tipping or accidental dislodgement of the prosthesis 10.

Figure 26:
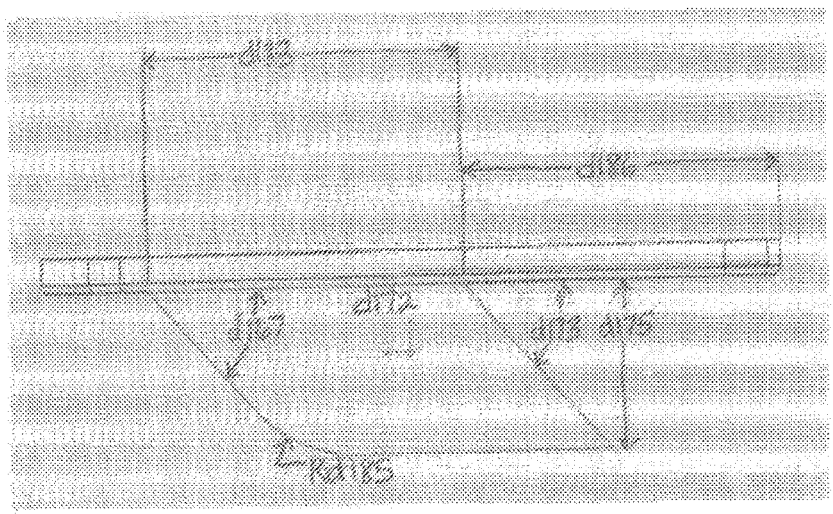
FIG. 26 is a side elevational view of a prosthesis according to the present invention showing generic keel dimensions.
Figure 27:
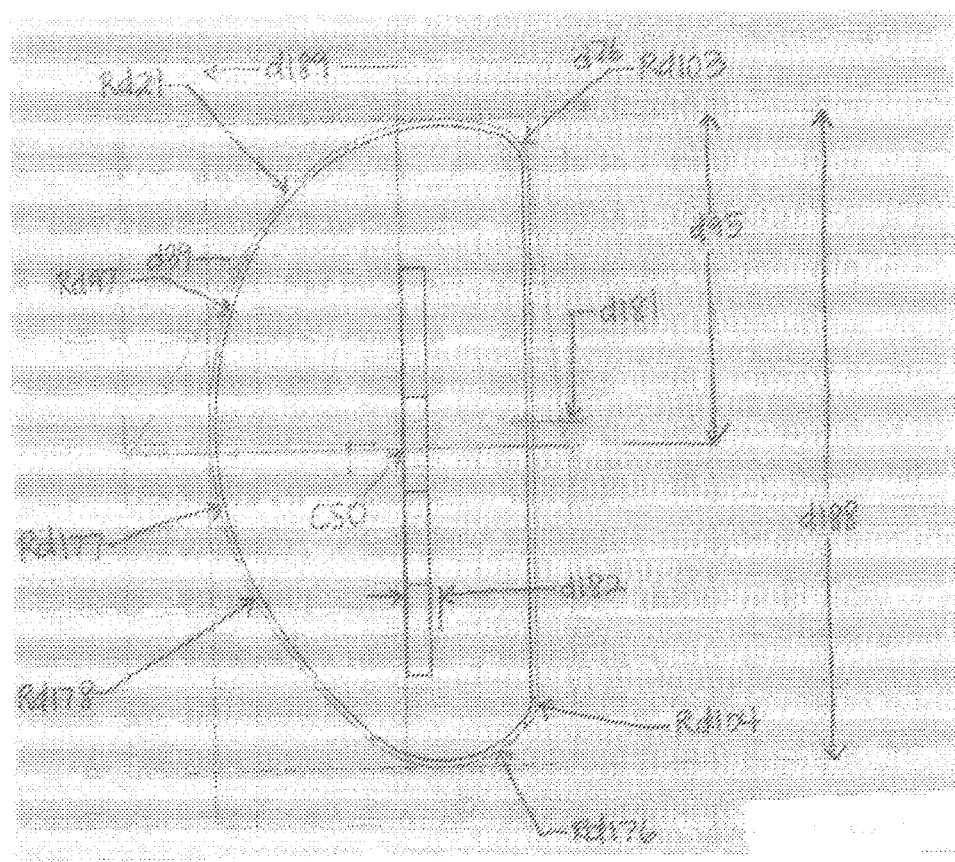
FIG. 27 is a bottom plan view of a prosthesis according to the present invention showing generic keel dimensions.

Turning now to FIGS. 26-27, a prosthesis 10 according to the present invention is illustrated with generic keel dimensions for a left medial knee prosthesis. The keel position may be described as a percentage of the length ahead of or behind the prosthesis centerline. The depth may be measured at the longest point as measured from the bottom face 14 of the prosthesis 10. A relationship table for the dimensions shown is provided below, where it is understood a change in these ratios by +1-25% or more is fully contemplated according to the present invention.

D188=Length
D29=0.367*D188
D76=0.224*D188
D95=0.510*D188
D97=0.694*D188
D103=0.061*D188
D104=0.061*D188
D176=0.204*D188
D177=0.510*D188
D178=0.735*D188
D181=0.041*D188
D182=0.061*D188
D189=0.551*D188
D183=0.429*D188
D186=0.429*D188
D175=0.200*D188

Figure 28:
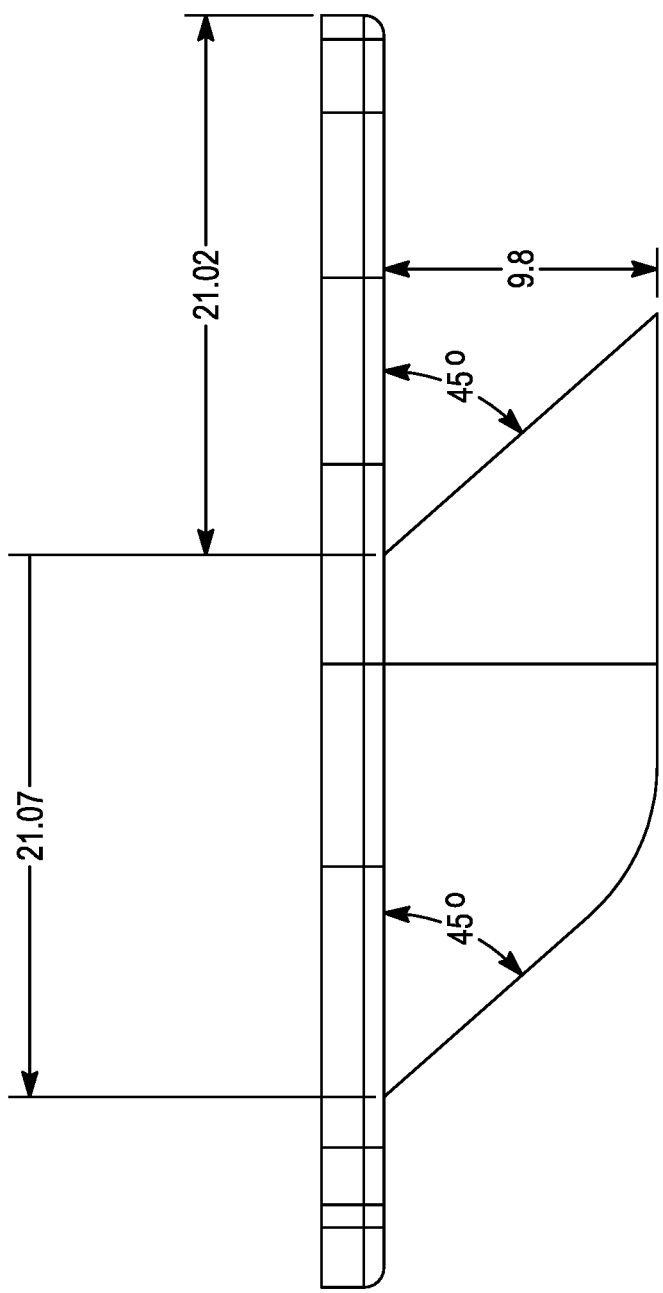
FIG. 28 is a side elevational view of a prosthesis according to the present invention showing exemplary keel dimensions.
Figure 29:
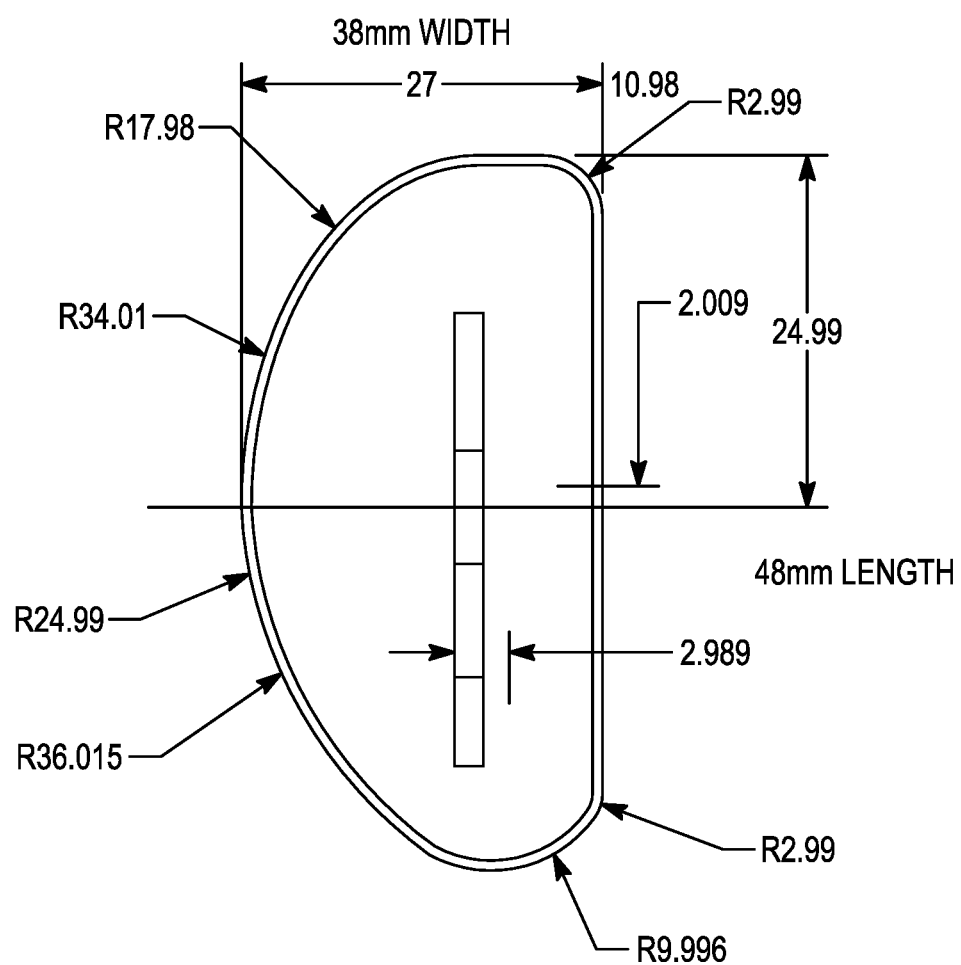
FIG. 29 is a bottom plan view of a prosthesis according to the present invention showing exemplary keel dimensions.
Figure 30:
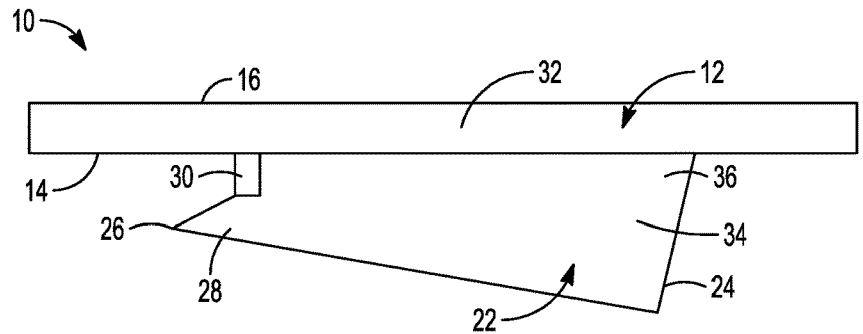
FIG. 30 is a side elevational view of a prosthesis according to the present invention including a keel with a hooked posterior end and a relatively longer, angled anterior end.
Figure 31:
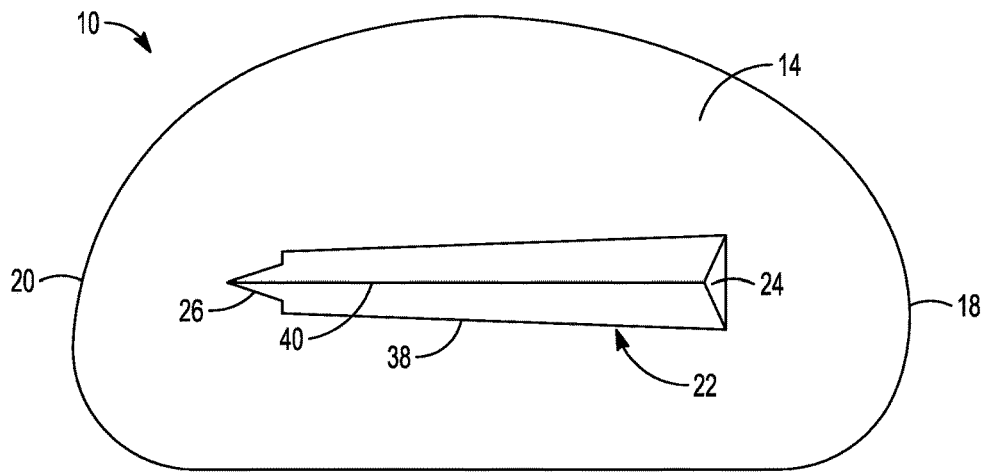
FIG. 31 is a bottom plan view of the prosthesis of FIG. 30.
Figure 32:
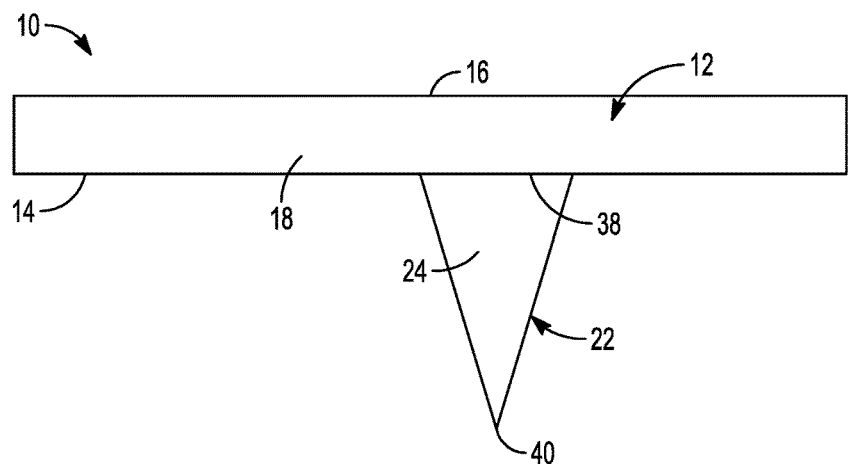
FIG. 32 is a front elevational view of the prosthesis of FIG. 30.
Figure 33:
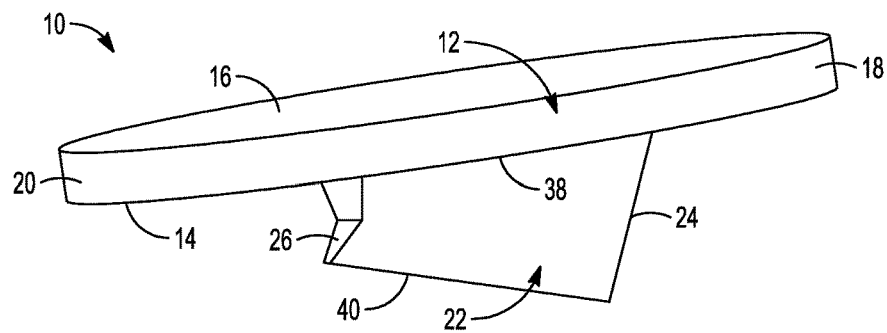
FIG. 33 is a rear perspective view of the prosthesis of FIG. 30.
Figure 34:
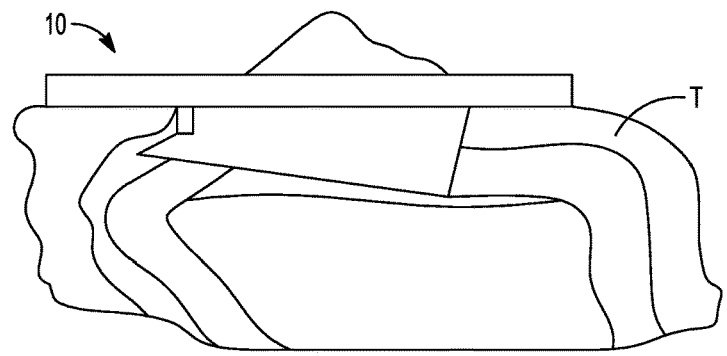
FIG. 34 is a side elevational view of the prosthesis of FIG. 30 shown with reference to a cross-section of a tibia, wherein a representative thickness subchondral and cortical bone are represented.

These ratios may describe the relative placement of the keel 22 on the prosthesis 10 (along the anterior-posterior and medial-lateral directions) and may apply to all keel embodiments shown and described herein, wherein the variations in the design of the keel itself are depicted in the drawings. FIGS. 28-29 illustrate possible dimensions for an exemplary prosthesis according to the present invention having a 49 mm length and 2 mm thickness. It is understood, of course, that the prosthesis 10 is not limited to this configuration.

Figure 35:
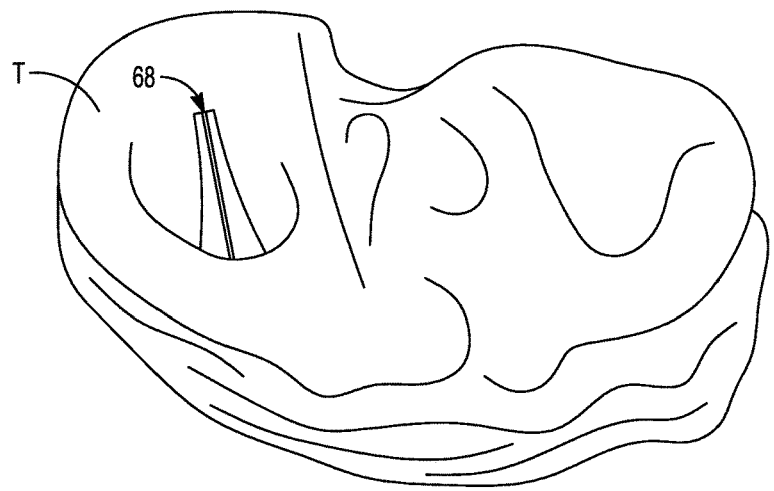
FIG. 35 is a top perspective view of a tibial cut which may be utilized for receiving the prosthesis of FIG. 30.
Figure 36:
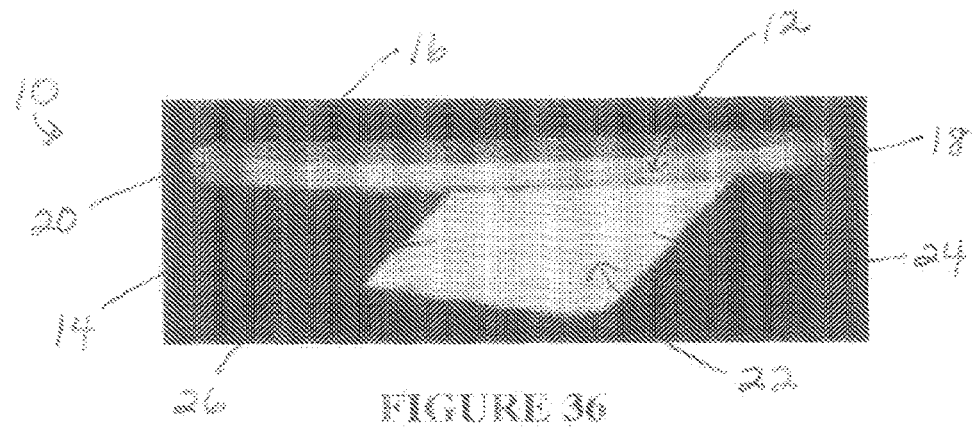
FIG. 36 is a side elevational view of a prosthesis according to the present invention including a keel with an angled posterior end and a relatively longer, rounded anterior end.
Figure 37:
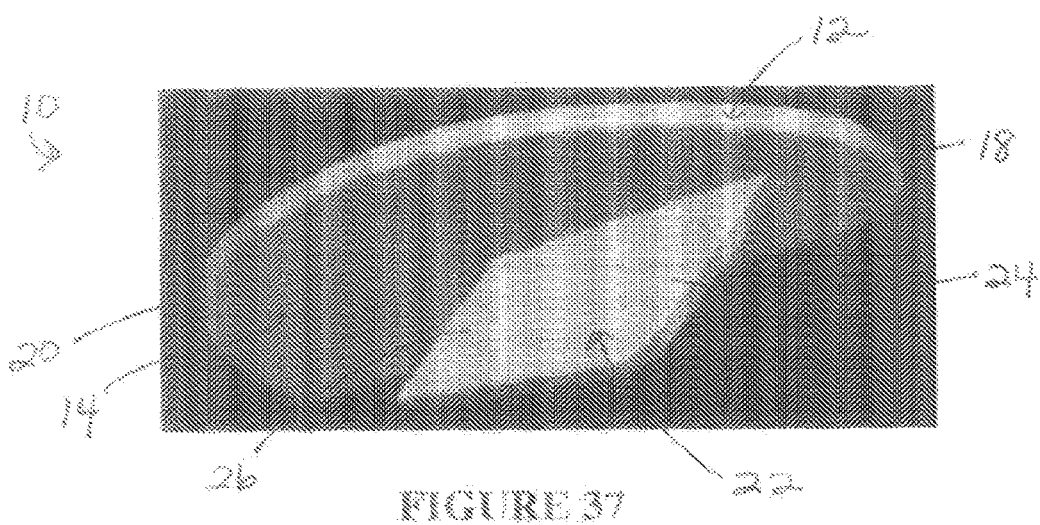
FIG. 37 is a bottom perspective view of the prosthesis of FIG. 36.
Figure 38:
FIG. 38 is a side elevational view of the prosthesis of FIG. 36 shown with reference to a cross-section of a tibia, wherein a representative thickness subchondral and cortical bone are represented.
Figure 39:
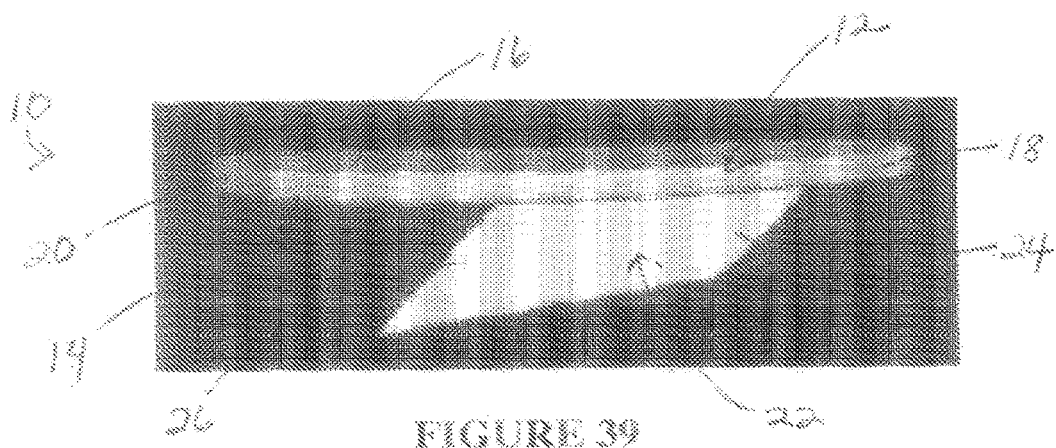
FIG. 39 is a side elevational view of a prosthesis according to the present invention including a keel with an angled posterior end and a relatively shorter, rounded anterior end.
Figure 40:
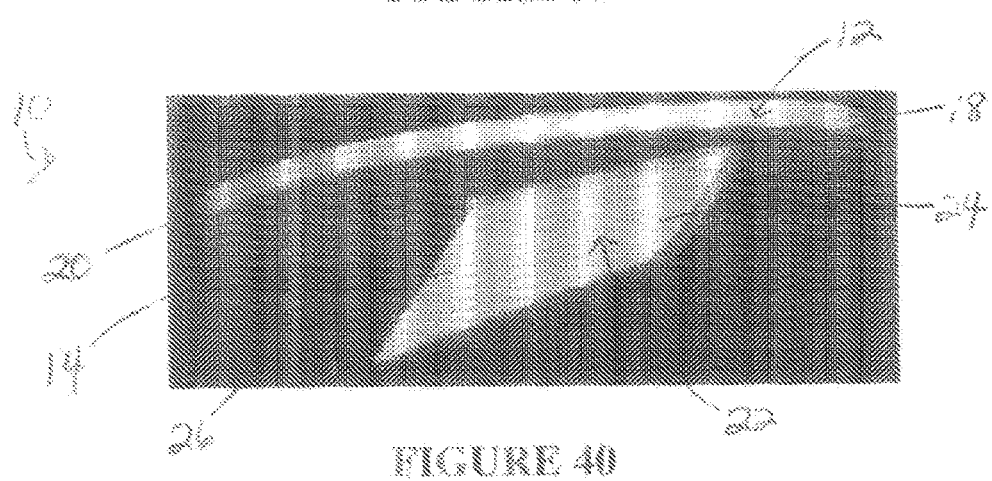
FIG. 40 is a bottom perspective view of the prosthesis of FIG. 39.
Figure 41:
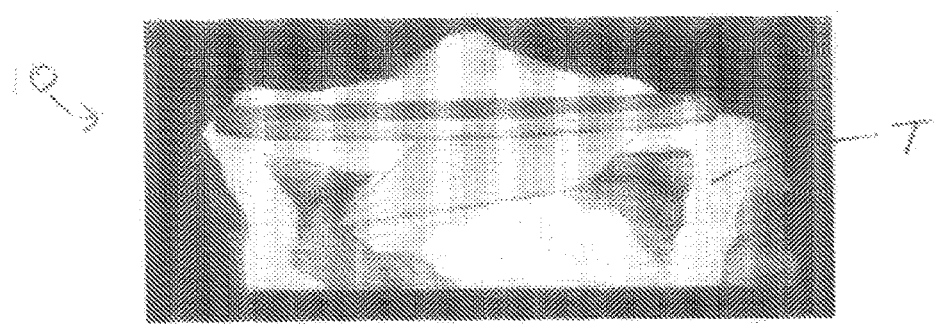
FIG. 41 is a side elevational view of the prosthesis of FIG. 39 shown with reference to a cross-section of a tibia, wherein a representative thickness subchondral and cortical bone are represented.

U.S. Pat. No. 6,966,928, incorporated by reference herein, describes a keel having a depth which tapers from one end of the prosthesis to another, such that the taper may be used to facilitate the insertion of the prosthesis. Such a tapered design may also be utilized with the prosthesis 10 according to the present invention. In particular, FIGS. 30-34 illustrate a prosthesis 10 including a keel 22 with a hooked posterior end 26 and a relatively longer, angled anterior end 24 such that the keel anterior end 24 extends longer distally compared with the keel posterior end 26. FIG. 35 is a top perspective view of a tibial cut 68 which may be utilized for receiving the prosthesis 10 of FIG. 30, FIGS. 36-38 depict a prosthesis 10 according to the present invention including a keel 22 with an angled posterior end 26 and a relatively longer, rounded anterior end 24. FIGS. 39-41 depict a prosthesis 10 according to the present invention including a keel 22 with an angled posterior end 26 and a relatively shorter, rounded anterior end 24, such that the keel posterior end 26 extends longer distally compared with the keel anterior end 24. In addition, the keel 22 in any embodiment depicted herein may taper in width from an end proximal to the prosthesis bottom face 14 to an end distal from the prosthesis bottom face 14 such that a proximal end 38 of the keel 22 is wider than a distal end 40 of the keel 22, creating a sort of knife edge which may facilitate insertion.

Figure 42:
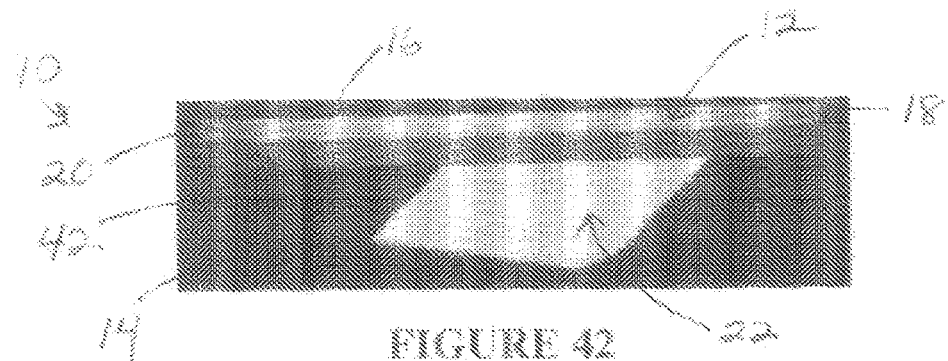
FIG. 42 is a side elevational view of a prosthesis according to the present invention including a keel with an angled posterior end and a relatively shorter, rounded anterior end, the prosthesis including a cushioning component on a tibial face thereof.
Figure 43:
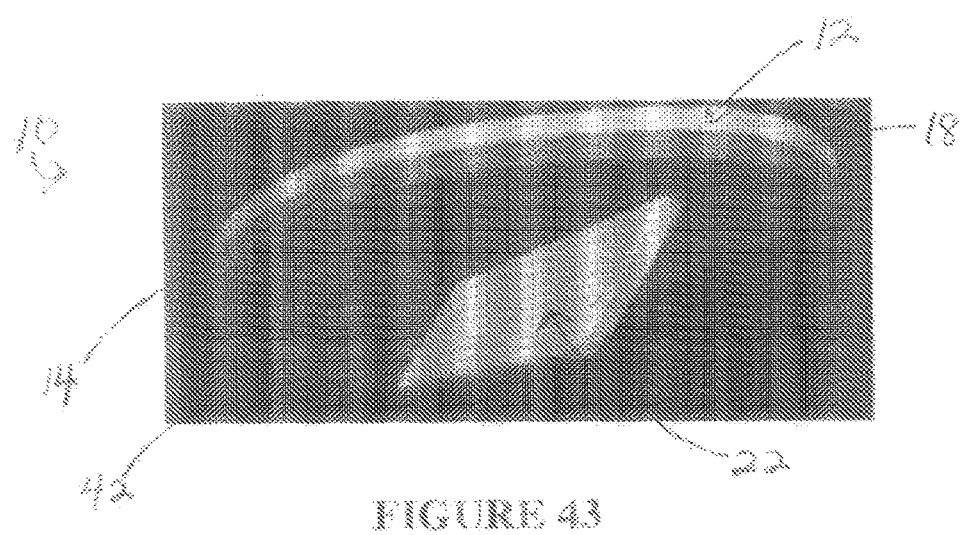
FIG. 43 is a bottom perspective view of the prosthesis of FIG. 42.
Figure 44:
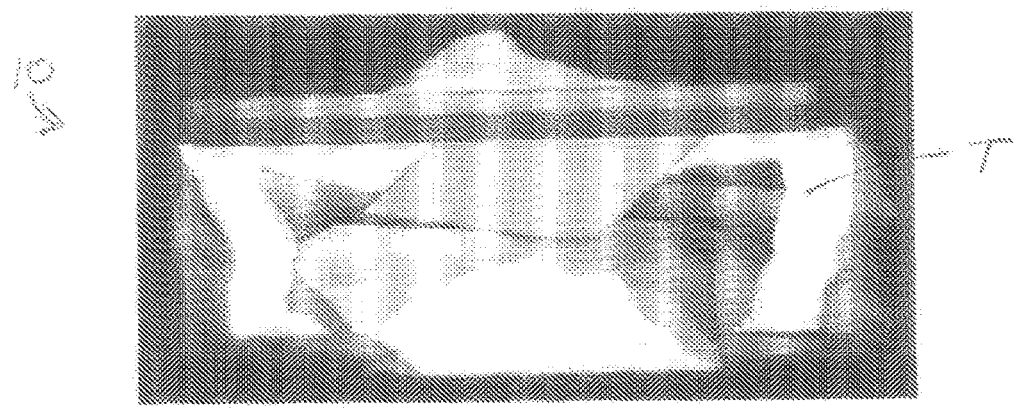
FIG. 44 is a side elevational view of the prosthesis of FIG. 42 shown with reference to a cross-section of a tibia, wherein a representative thickness subchondral and cortical bone are represented.

In accordance with the present invention, a thinner prosthesis may be used where the final intent is to cover at least one face of the base prosthesis with a load-absorbing, cushioning, or other surfacing component 42. As shown in FIGS. 42-44, one embodiment may utilize a hard articulating surface bearing material like metal, ceramic, or certain polymers (e.g., pyrolytic carbon or PEEK) which may include a surfacing component 42 provided on a bottom face 14 thereof wherein the surfacing component 42 then contacts the tibial plateau T, or alternatively is sandwiched between the outer articulating surface and an anchoring implant base. The load absorbing material may be a polymer or other material, such as a metallic sponge or springs. Biologically compatible urethanes, various hydrogels, and/or polymers that contain biologic components can also be utilized. It is also possible that one material can perform both the articulating function and the load absorbing function. According to one aspect of the present invention, the prosthesis configuration may allow for volume expansion of the surfacing component 42 while under load. The prosthesis 10 and the surfacing component 42 may be mechanically linked at the time of surgery to allow for surgeon selection of polymer thickness and material properties such as water content, durometer, viscoelastic behavior, and others. However, such a linkage is not necessary.

Figure 45:
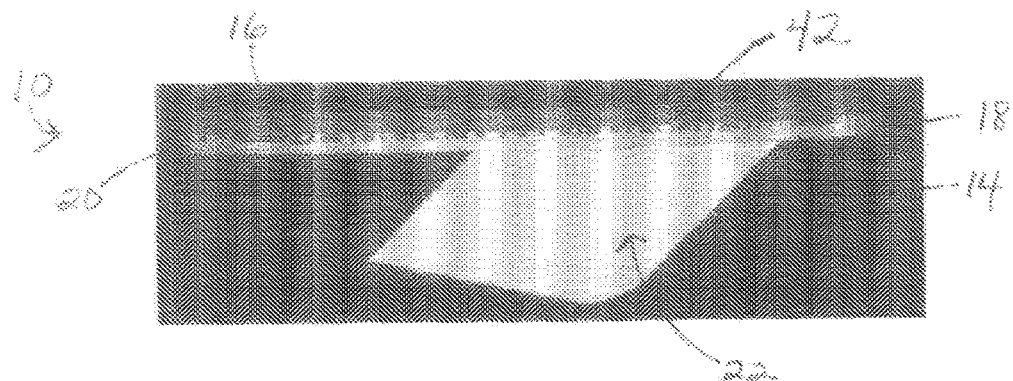
FIG. 45 is a side elevational view of a prosthesis according to the present invention including a keel with an angled posterior end and a relatively shorter, rounded anterior end, the prosthesis including a cushioning component on a femoral face thereof.
Figure 46:
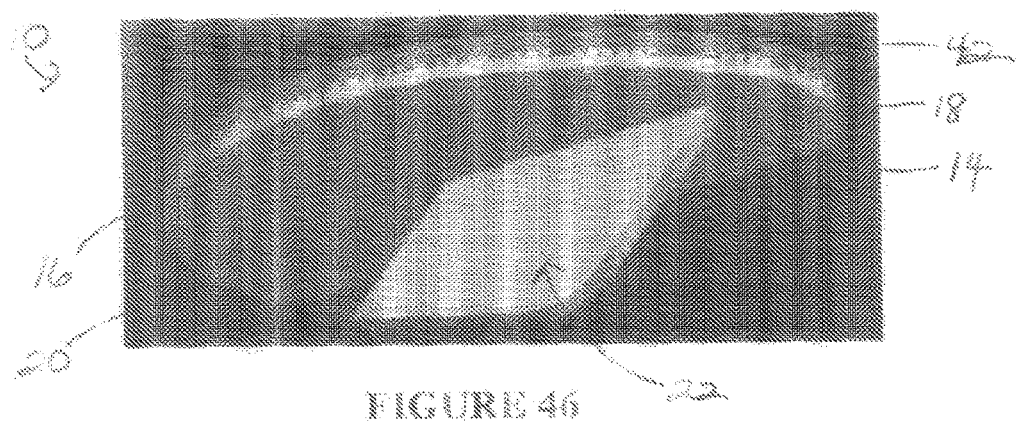
FIG. 46 is a bottom perspective view of the prosthesis of FIG. 45.
Figure 47:
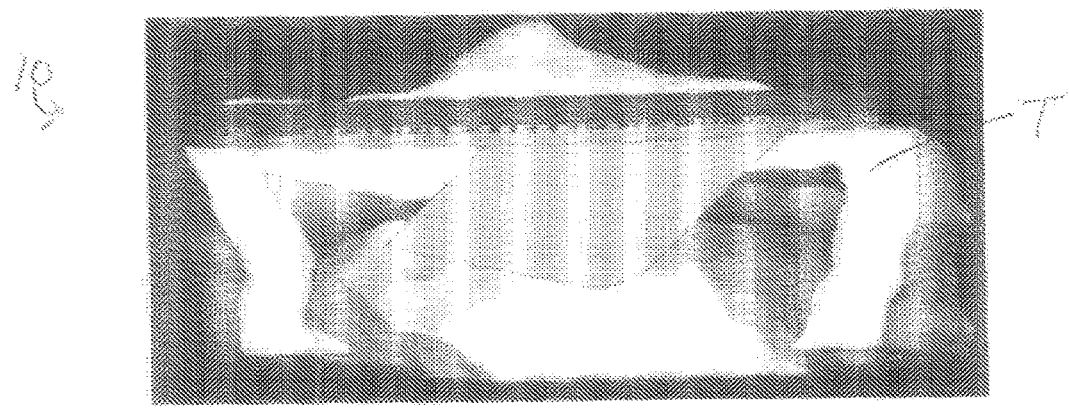
FIG. 47 is a side elevational view of the prosthesis of FIG. 45 shown with reference to a cross-section of a tibia, wherein a representative thickness subchondral and cortical bone are represented.
Figure 48:
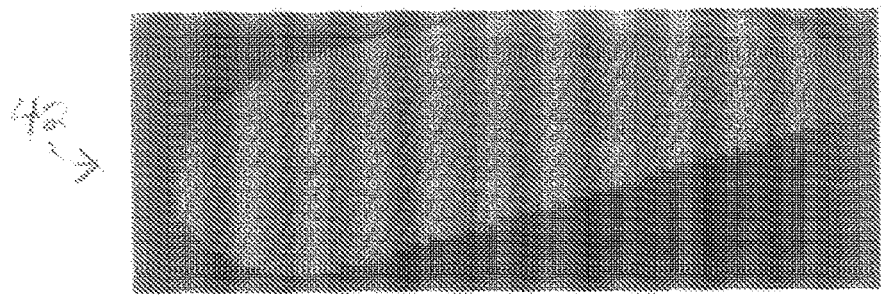
FIG. 48 is a bottom perspective view of a cushioning component according to the present invention.
Figure 49:
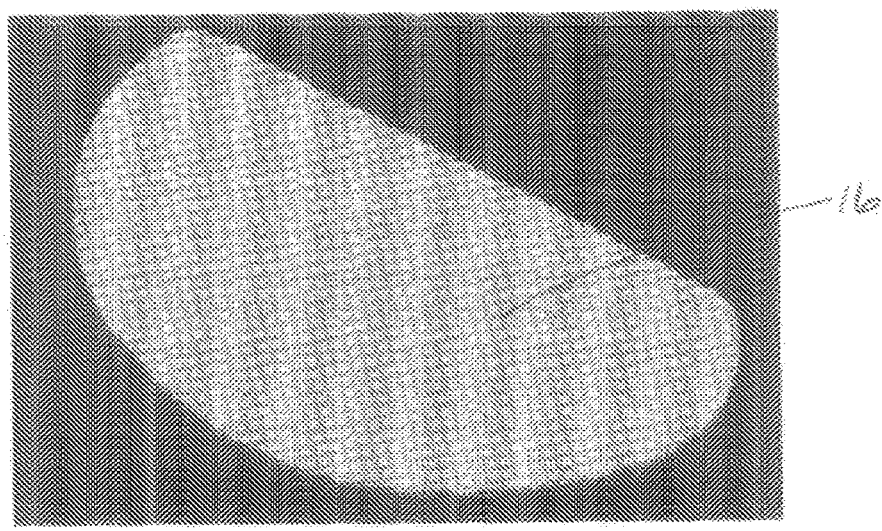
FIG. 49 is a top perspective view of a femoral face of the prosthesis of FIG. 45 which is prepared to receive a cushioning component thereon.
Figure 50:
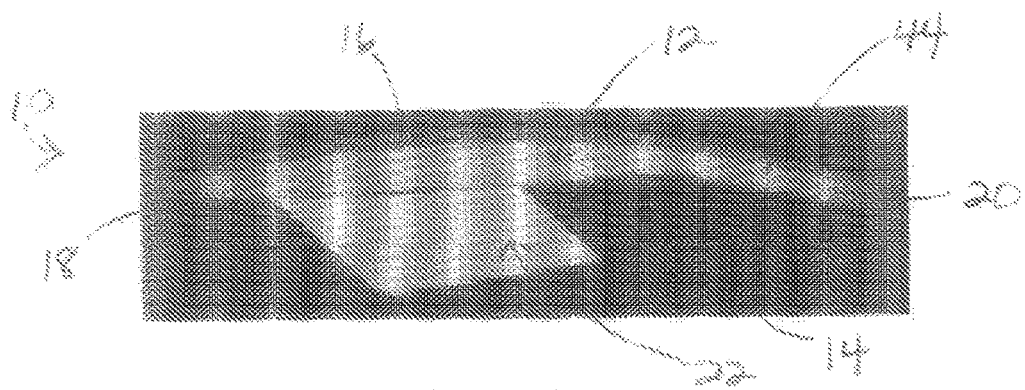
FIG. 50 is a side elevational view of a prosthesis according to the present invention which may be utilized for a lateral compartment implantation, the prosthesis including a keel having an angled posterior end and a relatively longer, angled anterior end.
Figure 51:
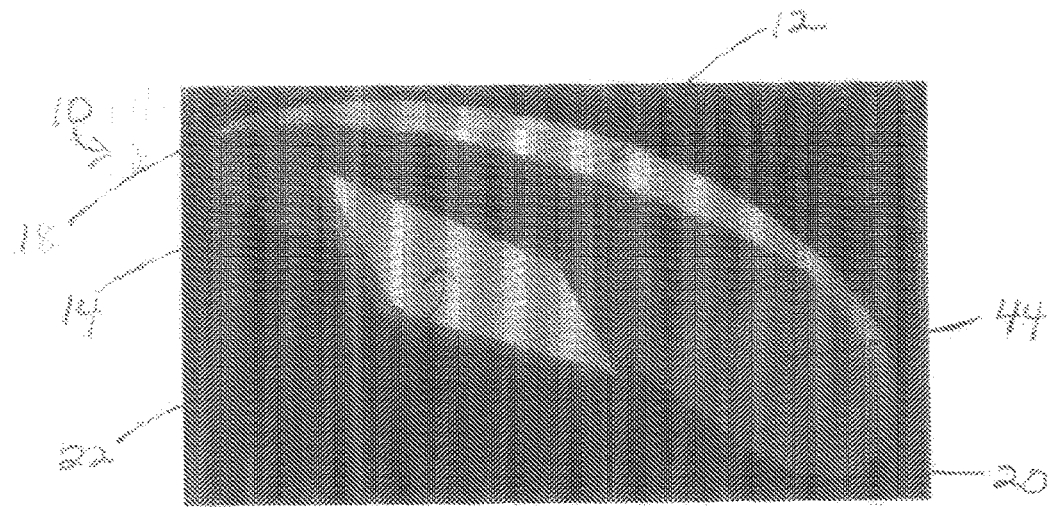
FIG. 51 is a bottom perspective view of the prosthesis of FIG. 50.
Figure 52:
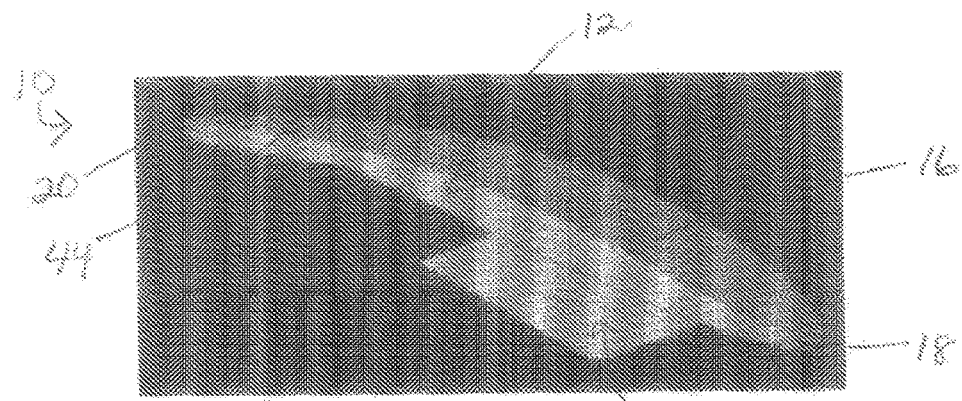
FIG. 52 is a top perspective view of the prosthesis of FIG. 50.
Figure 53:
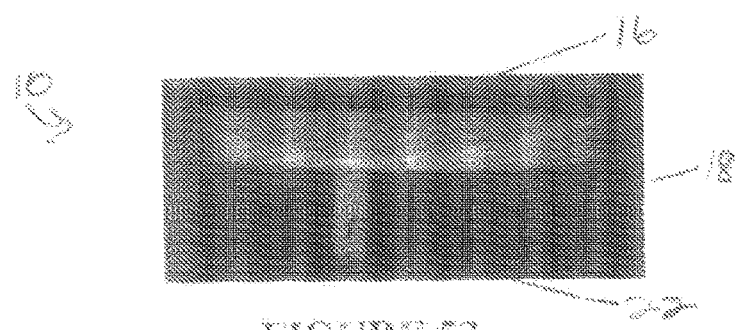
FIG. 53 is a front elevational view of the prosthesis of FIG. 50.
Figure 54:
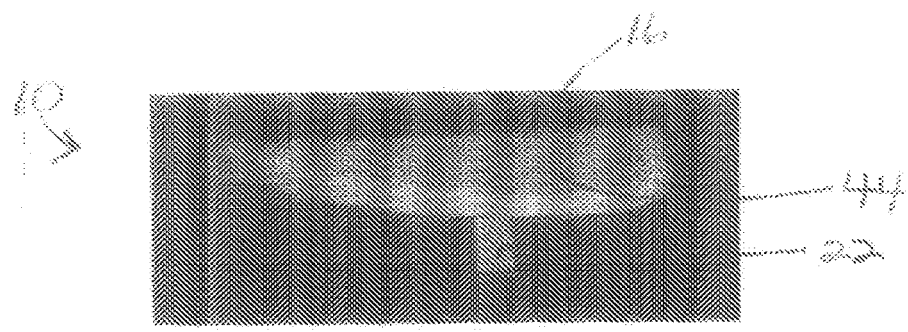
FIG. 54 is a rear elevational view of the prosthesis of FIG. 50.
Figure 55:
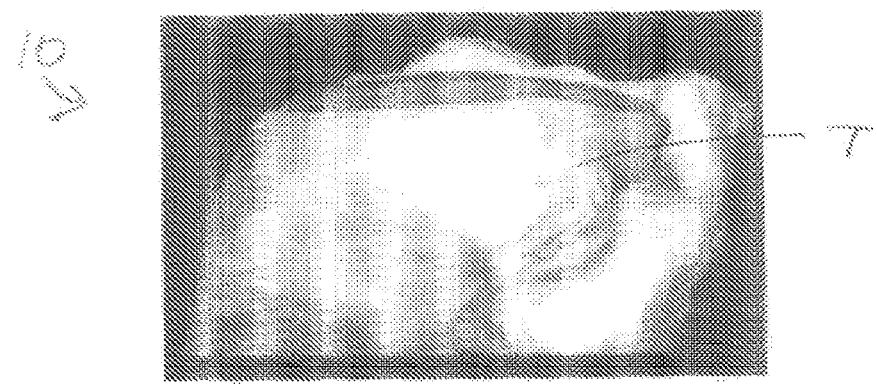
FIG. 55 is a side elevational view of the prosthesis of FIG. 50 shown with reference to a cross-section of a tibia, wherein a representative thickness subchondral and cortical bone are represented.

With reference to FIGS. 45-47, a prosthesis 10 according to the present invention is illustrated which includes a load absorbing, cushioning, or surfacing component 42 on a top face 16 thereof. In both this embodiment and that described above, a surface of the prosthesis 10 may be prepared mechanically and/or chemically to receive the surfacing component 42. For example, FIG. 48 illustrates a bottom perspective view of a surfacing component 42 according to the present invention, and FIG. 49 illustrates a top perspective view of a top face 16 of the prosthesis of FIG. 45 which is prepared to receive a surfacing component 42 thereon. In addition, the keel 22 itself could have a load absorbing, cushioning, or surfacing component associated therewith, such as to provide strain isolation.

With reference now to FIGS. 50-55, a prosthesis 10 according to the present invention is illustrated which may be utilized for a lateral compartment implantation. The prosthesis depicted includes a keel 22 having an angled posterior end 26 and a relatively longer, angled anterior end 24, although any of the keel 22 embodiments shown or described herein could alternatively be utilized. As shown, a posterior slope 44 may be provided on both the femoral and tibial faces 14, 16 of the prosthesis 10.

Figure 56:
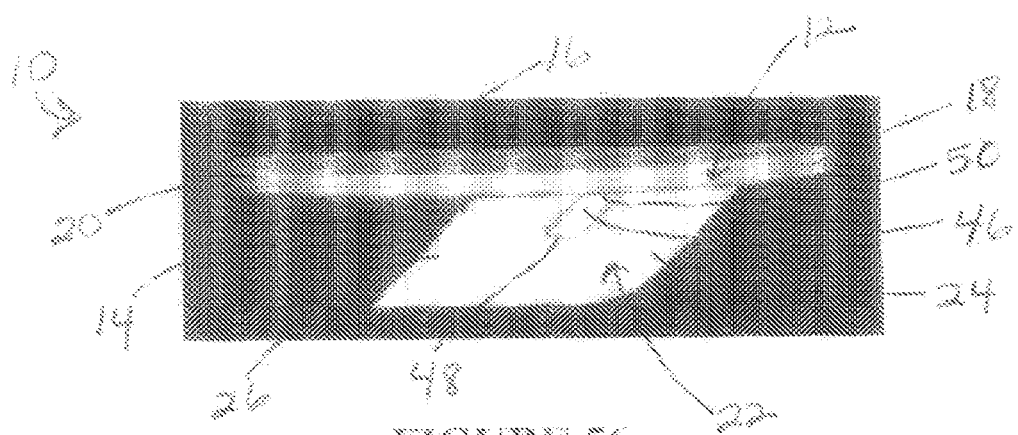
FIG. 56 is a side elevational view of a prosthesis according to the present invention including a keel with an angled posterior edge, a rounded anterior edge, and an angled cross-keel member.
Figure 57:
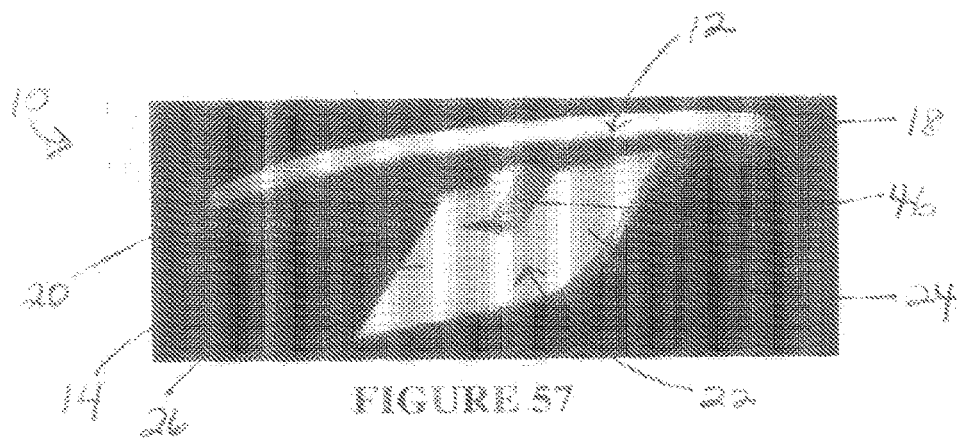
FIG. 57 is a bottom perspective view of the prosthesis of FIG. 56.
Figure 58:
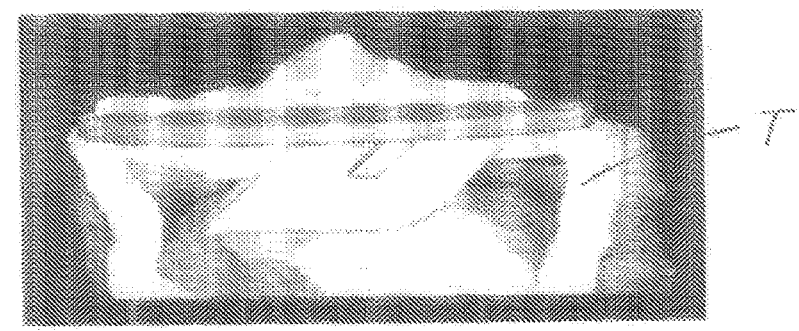
FIG. 58 is a side elevational view of the prosthesis of FIG. 56 shown with reference to a cross-section of a tibia, wherein a representative thickness subchondral and cortical bone are represented.
Figure 59:
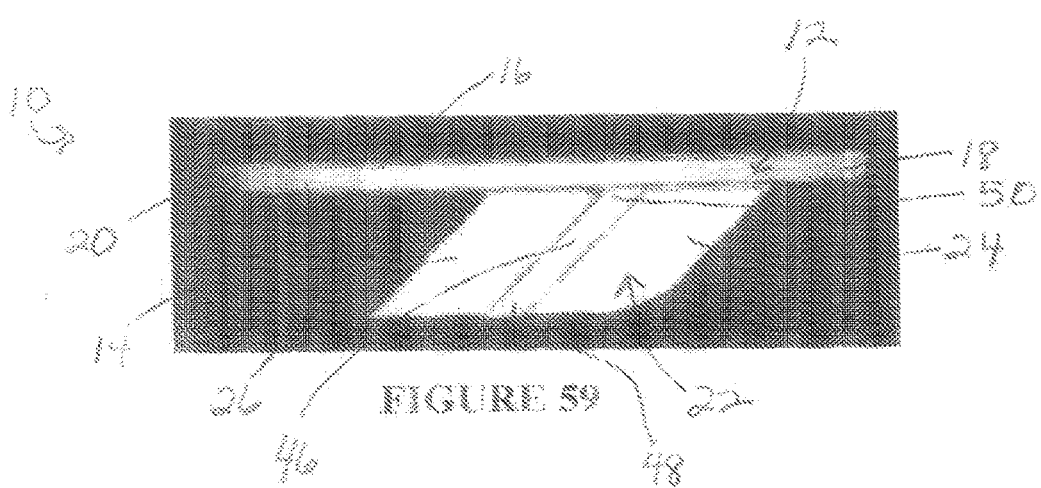
FIG. 59 is a side elevational view of a prosthesis according to the present invention including a keel with an angled posterior end, a rounded anterior end, and an angled cross-keel member extending the depth of the keel.
Figure 60:
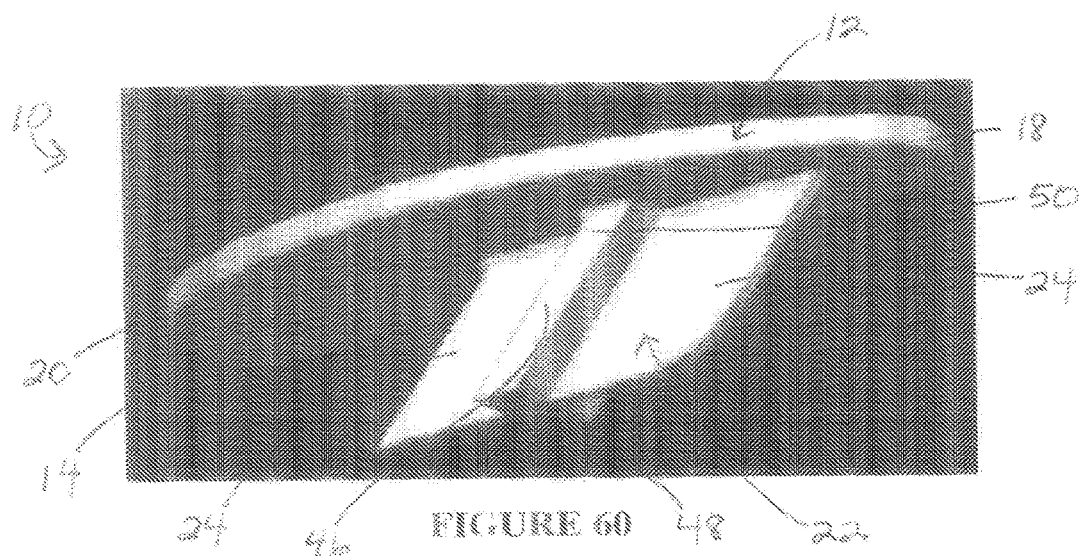
FIG. 60 is a bottom perspective view of the prosthesis of FIG. 59.
Figure 61:
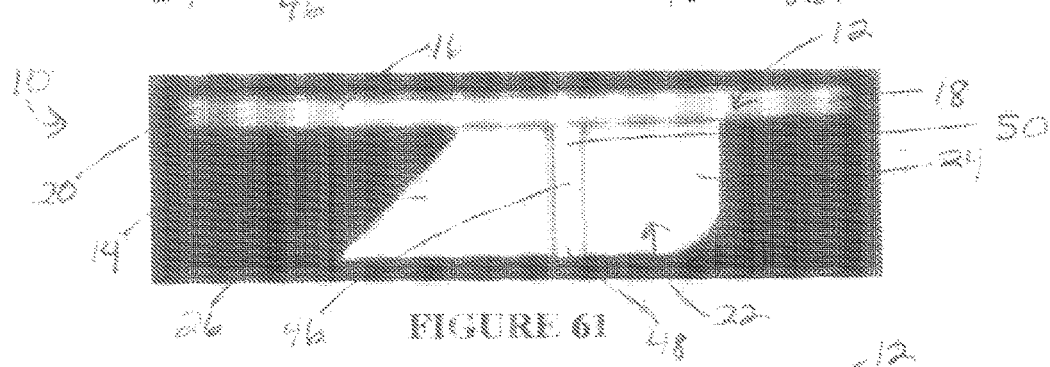
FIG. 61 is a side elevational view of a prosthesis according to the present invention including a keel with an angled posterior end, a rounded anterior end, and a cross-keel member extending along the depth of the keel.
Figure 62:
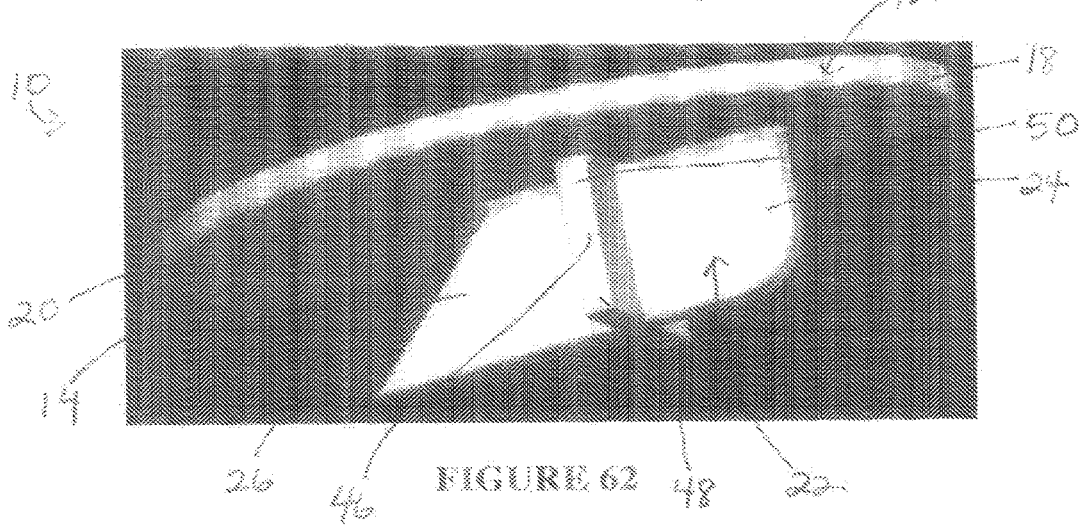
FIG. 62 is a bottom perspective view of the prosthesis of FIG. 61.
Figure 63:
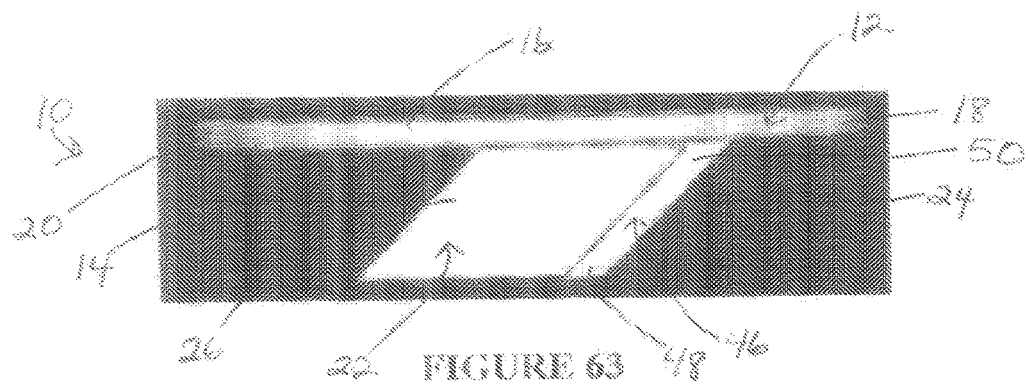
FIG. 63 is a side elevational view of a prosthesis according to the present invention including a keel with an angled posterior end, an angled anterior end, and an angled cross-keel member extending along the depth of the keel at the anterior end.
Figure 64:
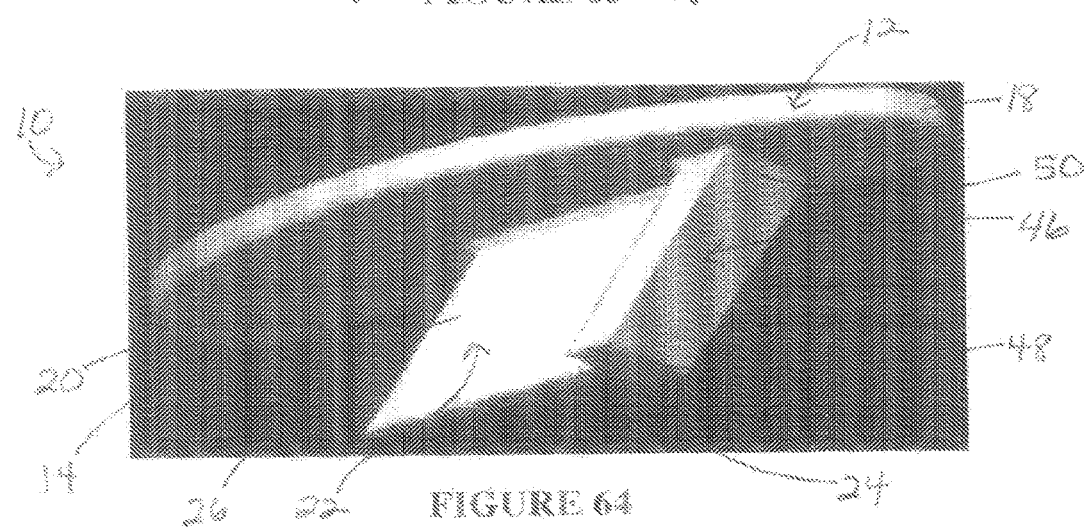
FIG. 64 is a bottom perspective view of a prosthesis of FIG. 63.
Figure 65:
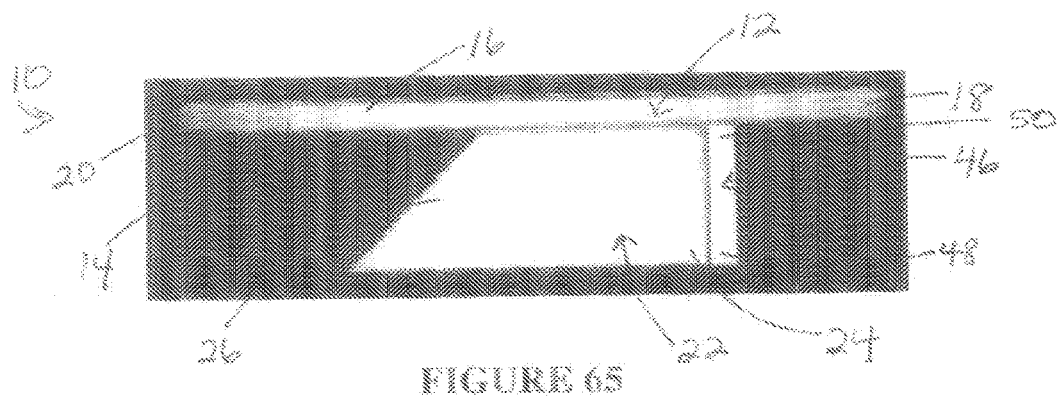
FIG. 65 is a side elevational view of a prosthesis according to the present invention including a keel with an angled posterior end, an anterior end generally orthogonal to a bottom face of the prosthesis, and a cross-keel member extending along the depth of the keel at the anterior end.
Figure 69:
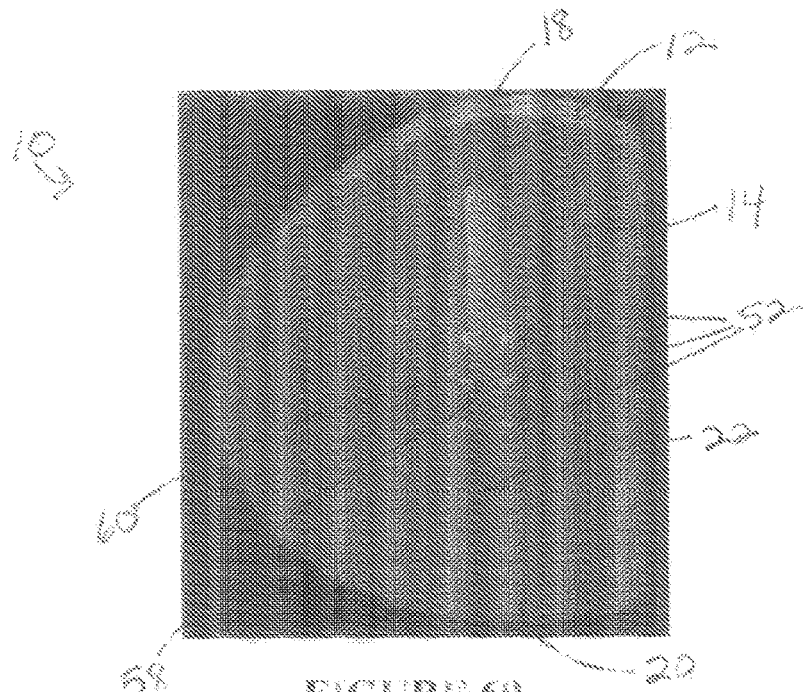
FIG. 69 is a bottom plan view of the prosthesis of FIG. 67.
Figure 70:
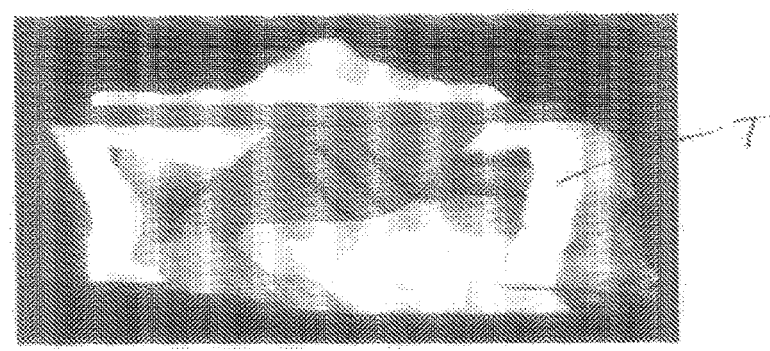
FIG. 70 is a side elevational view of the prosthesis of FIG. 67 shown with reference to a cross-section of a tibia, wherein a representative thickness subchondral and cortical bone are represented.
Figure 71:
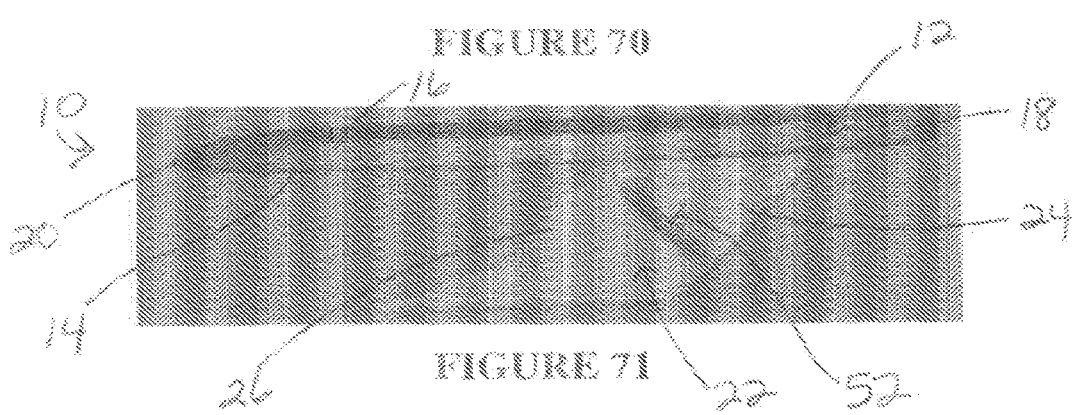
FIG. 71 is a side elevational view of a prosthesis according to the present invention including a keel with a hooked posterior end, a rounded, angled anterior end, and an angled barb member oriented toward the anterior end.
Figure 75:
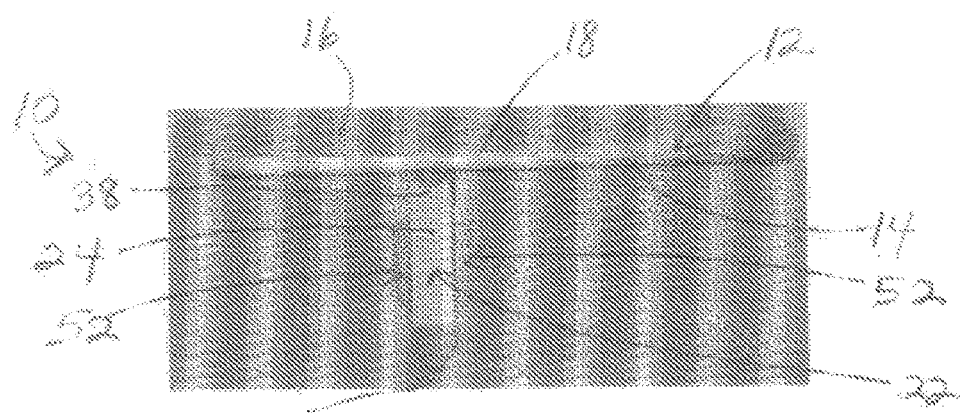
FIG. 75 is a rear elevational view of the prosthesis of FIG. 73.
Figure 76:
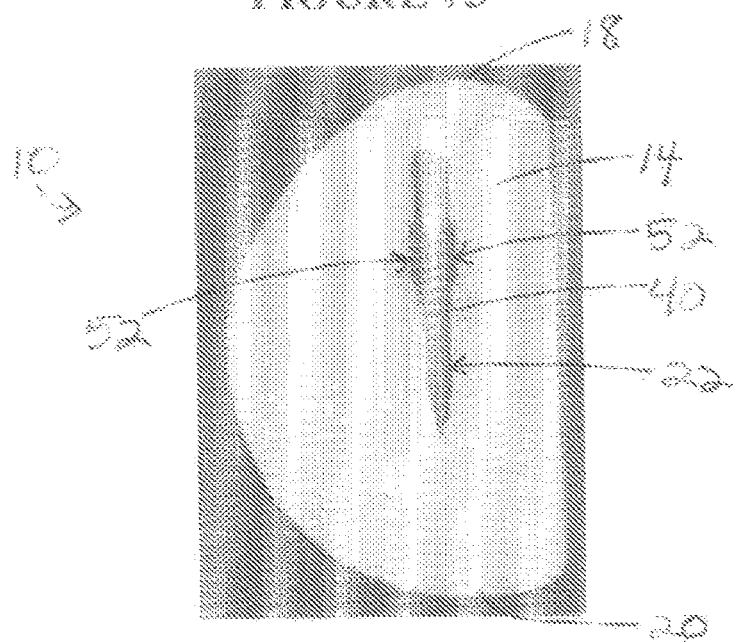
FIG. 76 is a bottom plan view of the prosthesis of FIG. 73.
Figure 77:
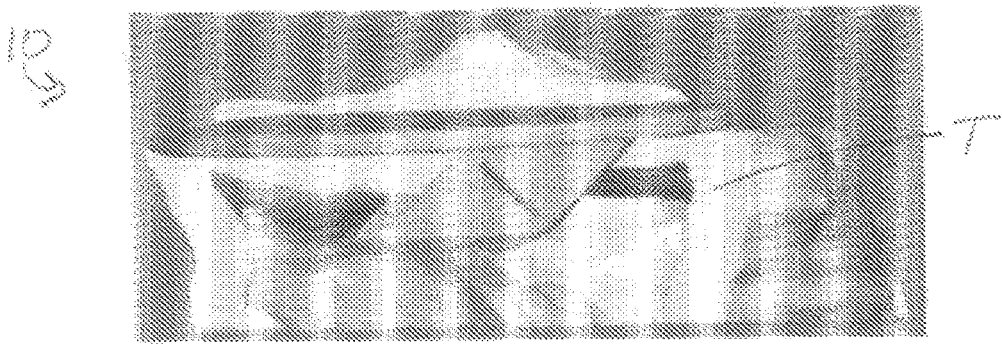
FIG. 77 is a side elevational view of the prosthesis of FIG. 73 shown with reference to a cross-section of a tibia, wherein a representative thickness subchondral and cortical bone are represented.

The prosthesis 10 according to the present invention may also include a cross-keel 46 provided generally in the medial-lateral (ML) direction, wherein cross-keel 46 may have a shorter length in the ML direction than does keel 22 in the AP direction. Such a cross-keel 46 may enhance the stability of the prosthesis 10 once inserted. The cross-keel 46 may be generally rectangular in shape, but is not limited as such. FIGS. 56-58 illustrate a prosthesis 10 according to the present invention including a keel 22 with an angled posterior end 26, a rounded anterior end 24, and a cross-keel 46 positioned at approximately the midpoint of the keel 22 in the AP direction, wherein the cross-keel 46 extends approximately ½ the depth of the keel 22. In this case, cross-keel member 46 has an angle which is similar to the angle of the keel posterior end 26, wherein a distal portion 48 of the cross-keel 46 extends farther toward the body posterior end 20 compared with a proximal portion 50 of the cross-keel 46. Of course, other depths and orientations of cross-keel 46 as compared with keel 22 are also contemplated. FIGS. 59-60 depict a prosthesis 10 according to the present invention including a keel 22 with an angled posterior end 26, a rounded anterior end 24, and an angled cross-keel 46 extending to approximately the same distal depth as the keel 22. FIGS. 61-62 illustrate a prosthesis 10 according to the present invention including a keel 22 with an angled posterior end 26, a rounded anterior end 24, and a cross-keel member 46 extending along the depth of the keel 22 generally orthogonal to the prosthesis bottom face 14. FIGS. 63-64 depict a prosthesis 10 according to the present invention including a keel 22 with an angled posterior end 26, an angled anterior end 24, and an angled cross-keel member 46 extending along the depth of the keel 22 at the anterior end 24. FIGS. 65-66 illustrate a prosthesis 10 according to the present invention including a keel 22 with an angled posterior end 26, an anterior end 24 extending distally generally orthogonal to bottom face 14, and a cross-keel member 46 extending along the depth of the keel 22 at the anterior end 24 generally orthogonal to the prosthesis bottom face 14.

The prosthesis 10 according to the present invention may also include shorter cross-keels or barb members 52 protruding from keel 22 generally in the ML direction. For example, FIGS. 67-70 illustrate a prosthesis 10 according to the present invention including a keel 22 with an angled posterior end 26, a rounded, angled anterior end 24, and a plurality of angled barb members 52 having an orientation generally orthogonal to the angle of the posterior end 26, where each barb member 52 has a distal portion 54 that extends farther toward the body anterior end 18 compared with a proximal portion 56 of the barb member 52. Barb members 52 may be tapered such that an end 58 adjacent the keel 22 is wider compared with an end 60 removed from the keel 22. In another embodiment, a single angled barb member 52 may be utilized as in FIGS. 71-77. In this example, the prosthesis 10 may include a keel 22 with a hooked posterior end 26 and a rounded, angled anterior end 24, although it is understood that barb members 52 may be used with any keel design shown or described herein. As illustrated in FIGS. 73-77, the keel 22 may taper so as to be more narrow at an end 40 thereof distal from the prosthesis bottom face 14 such that the bottommost portion of the keel 22 may be sharpened, which may be helpful in the downward and backward motion used to insert the prosthesis 10. The hooked posterior end 26 may also taper to a three-sided point. This configuration may help facilitate securing the prosthesis 10 and capturing SC hone. According to one aspect of the present invention, the more proximal portion 30 of the posterior end 26 may remain flat in order to avoid an upward cutting capability of the prosthesis 10 once inserted.

Figure 78:
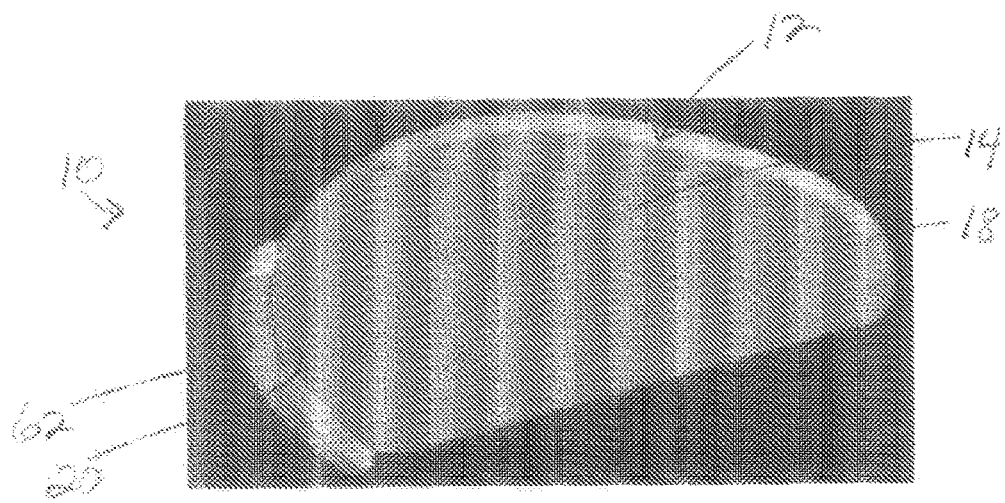
FIG. 78 is a bottom perspective view of a prosthesis according to the present invention including a posterior tab, wherein the keel is omitted for clarity.
Figure 79:
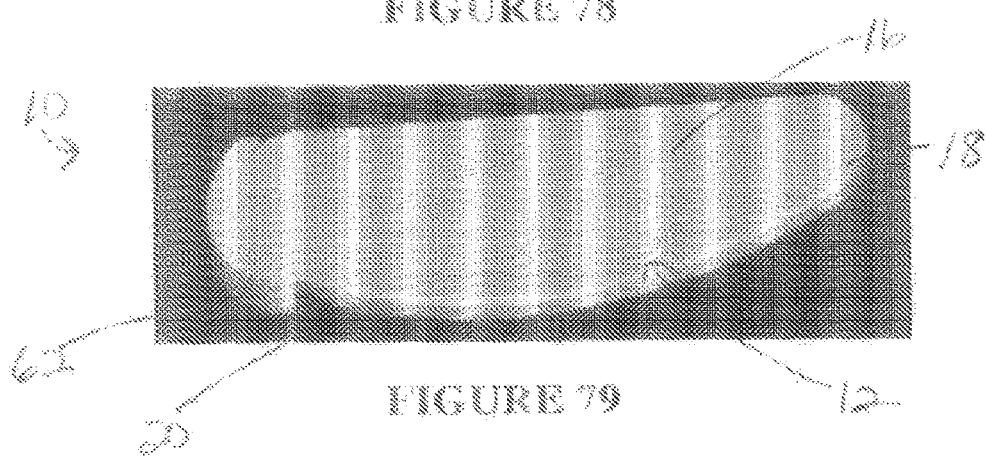
FIG. 79 is a top perspective view of the prosthesis of FIG. 78.
Figure 80:
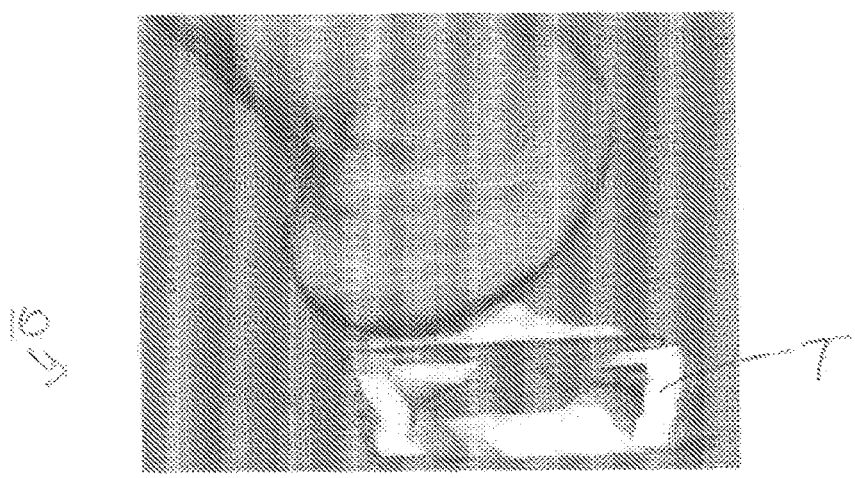
FIG. 80 is a side elevational view of the prosthesis of FIG. 78 including a keel similar to FIG. 73 and shown with reference to a cross-section of a tibia, wherein a representative thickness subchondral and cortical bone are represented.

In further accordance with the present invention, FIGS. 78-80 illustrate a prosthesis 10 including a posterior tab 62 provided at body posterior end 20 and extending distally beyond tibial face 14 which may be used to provide further stability to the prosthesis 10 once seated on the tibial plateau T. It is understood that the posterior tab 62 may have any shape or depth suitable for implantation, and is not limited to the configuration depicted herein.

The gap between the femoral condyle and the tibial plateau, after the plateau has been prepared, determines the allowable size and particular shape of the prosthesis that can be fit into this space. The location of the keel on the prosthesis, the angle of the keel, and the overall length and/or depth of the keel may determine the allowable insertion angle and thus the overall thickness of the prosthesis, where too large a keel or too posterior a keel location may prevent insertion of the prosthesis. To solve this problem, a deformable keel 22 could be utilized. Alternatively, a short depth (e.g., 2-3 mm) keel 22 could be used. In this case, once the prosthesis 10 is located in position, screws may be placed down through the interior of the keel 22 for final fixation.

Figure 81:
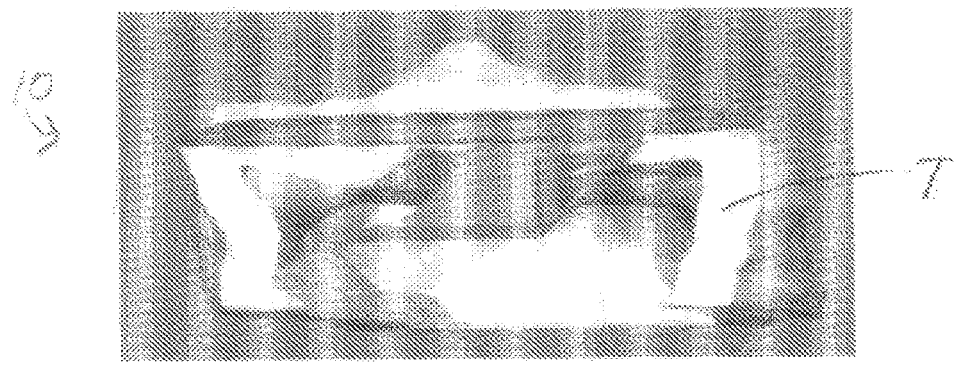
FIG. 81 is a side elevational view of a prosthesis according to the present invention including a keel with an expandable portion in the medial-lateral direction, wherein the prosthesis is shown with reference to a cross-section of a tibia, wherein a representative thickness subchondral and cortical bone are represented.
Figure 82:
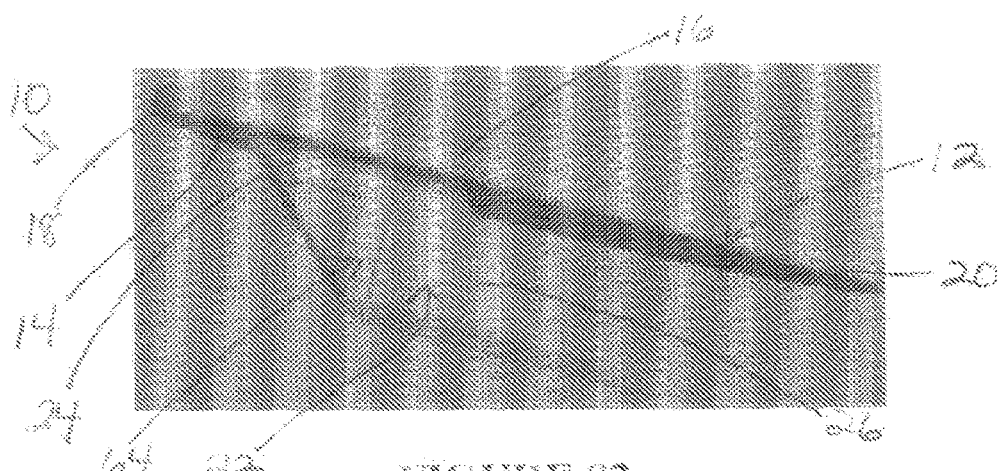
FIG. 82 is a bottom perspective view of the prosthesis of FIG. 81.
Figure 83:
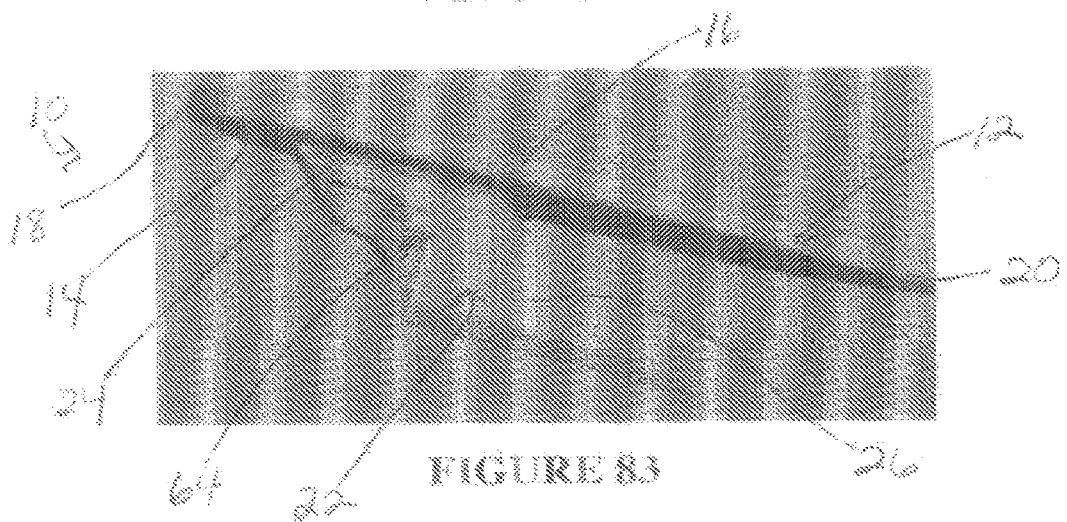
FIG. 83 is a bottom perspective view of the prosthesis of FIG. 81 with the expandable portion actuated.
Figure 84:
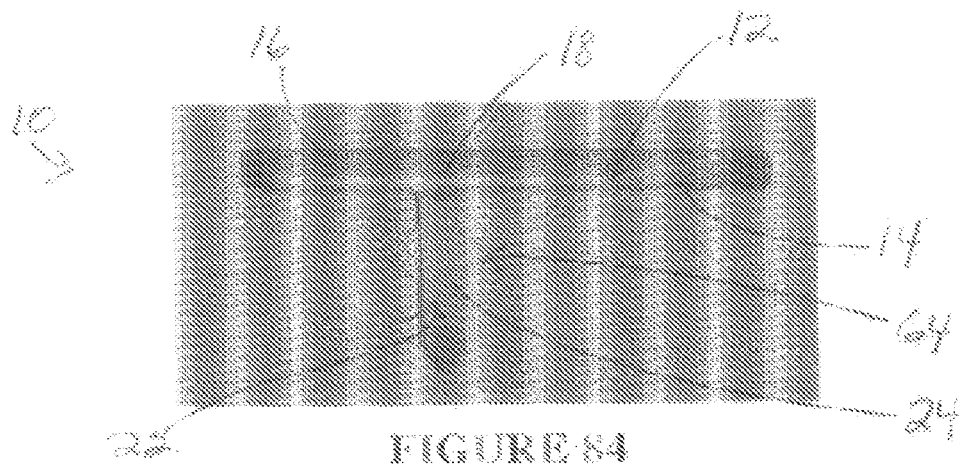
FIG. 84 is a rear elevational view of the prosthesis of FIG. 83.

As described above, a keel that is integral with the prosthesis body may be limited in length due to insertion issues. A post or screw may be added to the prosthesis, such as by threading it through the prosthesis body, once the prosthesis is in position. "Captured" screws have a lower tapered threaded portion for grabbing the bone and an upper portion with a machined thread for attaching to the prosthesis body during the last portion of travel of the screw into the bone, allowing for additional stability for the prosthesis. Strain isolation bushings may be added between the prosthesis and the screw to further isolate the screw from any strain induced by micromotion of the prosthesis. According to one aspect of the present invention, a modular keel assembly could be implemented, where a greater depth keel may be inserted once a short depth keel prosthesis is in place. This approach has the added advantage of customized fits for an individual patient's needs. In yet another embodiment, the prosthesis 10 may include an expandable keel portion 64 such as, but not limited to, an anterior portion as depicted in FIGS. 81-82. Once the prosthesis 10 is in place, a push pin or other actuator could be advanced through an internal slot in the prosthesis 10 to flare out the expandable keel portion 64 in the ML direction for additional capture as depicted in FIGS. 83-84.

Figure 85:
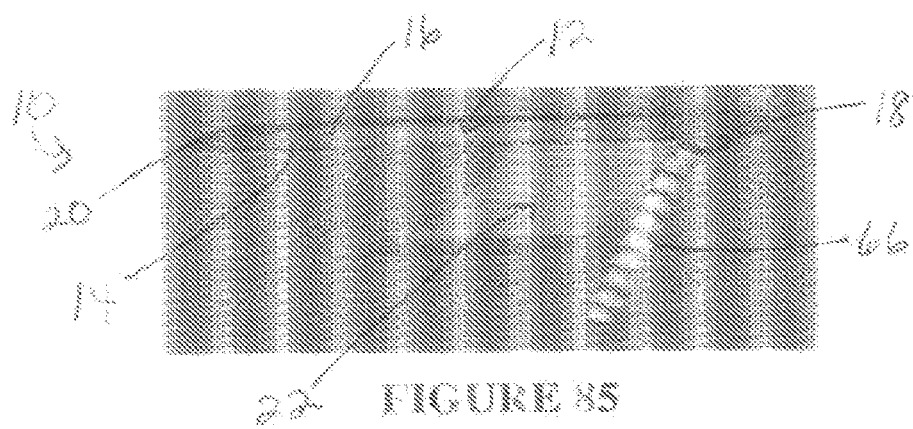
FIG. 85 is a side elevational view of a prosthesis according to the present invention including a keel and a screw for additional fixation.
Figure 86:
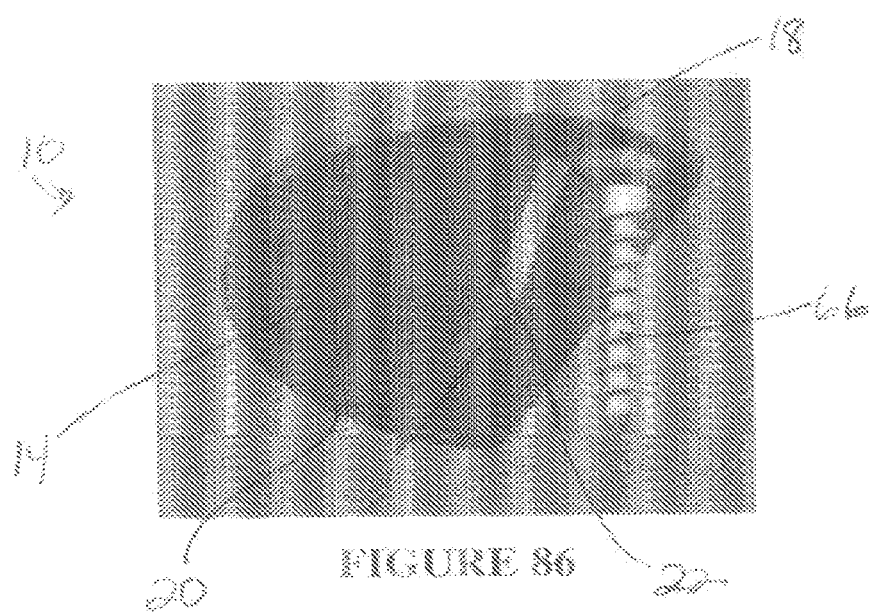
FIG. 86 is a bottom perspective view of the prosthesis of FIG. 85.
Figure 87:
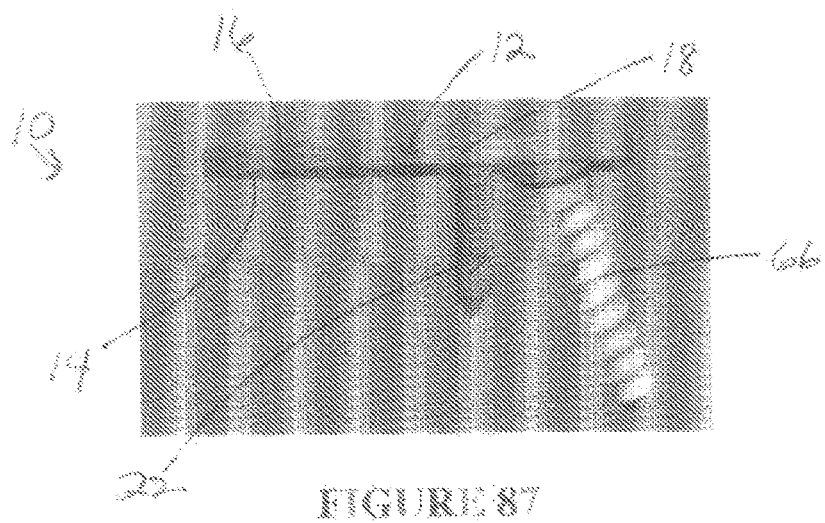
FIG. 87 is a front elevational view of the prosthesis of FIG. 85.

According to the present invention, at least a portion of the keel 22, especially those portions that will ultimately reside in cancellous bone, can be coated to promote bony in-growth or left smooth to discourage it. The keel 22 may include one or more openings therein. The prosthesis 10 according to the present invention could be screwed in, or have any type of fixation (e.g., cement) for additional stability. For example, with reference to FIGS. 85-87, a screw 66 or other fastener may be provided at the anterior-lateral corner of the prosthesis 10, and may be angled roughly 30 degrees downward off of the plane of the tibial plateau and 30 degrees from the AP direction of the keel 22, laterally (towards the tibial eminence). Of course, a screw or screws 66 are not limited to this position or orientation with respect to the prosthesis 10.

Figure 88:
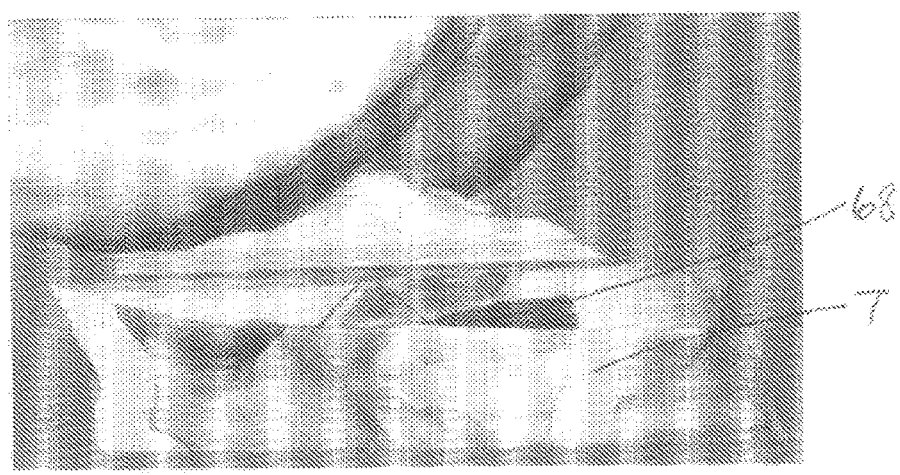
FIG. 88 is a cross-sectional view of the tibia showing a tibial cut therein and interaction of the flexed femur with the tibia.
Figure 89:
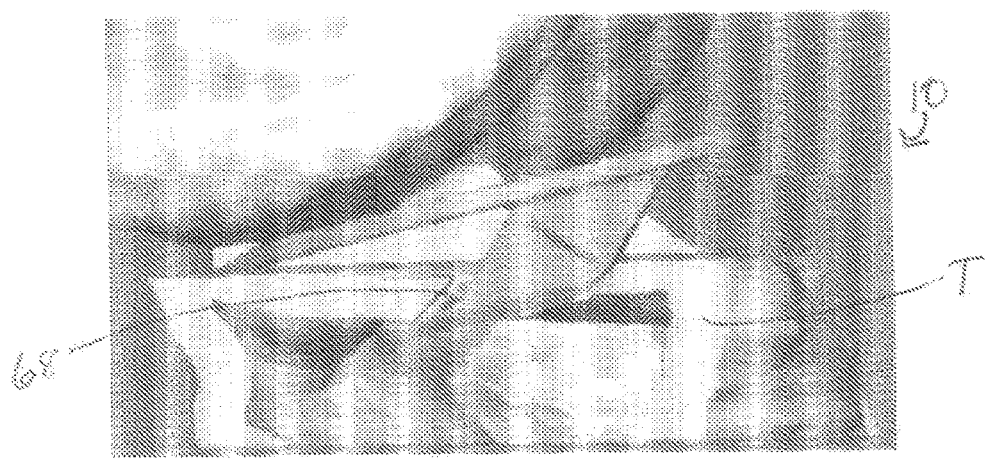
FIG. 89 is a side elevational view of the prosthesis of FIG. 73 as it is inserted into the tibial cut illustrated in FIG. 88.
Figure 90:
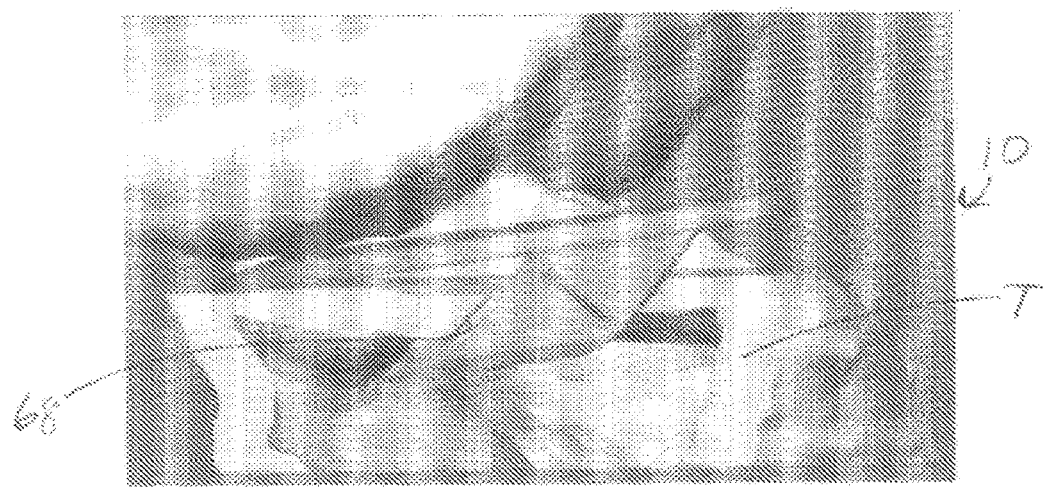
FIG. 90 is a side elevational view of the prosthesis of FIG. 73 upon further insertion into the tibial cut illustrated in FIG. 88.
Figure 91:
FIG. 91 is a side elevational view of the prosthesis of FIG. 73 upon complete insertion into the tibial cut illustrated in FIG. 88.

FIG. 88 is a cross-sectional view of the tibia T showing a tibial cut 68 therein and interaction of the femur with the tibia T, and FIGS. 89-91 illustrate the prosthesis of FIG. 73 as it is inserted into the tibial cut 68. As shown, the prosthesis 10 may be inserted at approximately a 45 degree angle and, in theory, could only be potentially dislodged via the same path. However, were the prosthesis 10 to come upward and forward, the femur in extension would push the prosthesis back into place, thus providing inherent stability.

The prosthesis 10 according to the present invention can be a monolithic design or may be made of two or more separate components. By utilizing a modular design, the physician may be able to draw from a library of components at the time of surgery that may adhesively, mechanically, magnetically, or otherwise cooperate with each other to yield an assembled prosthesis particularly suited for that particular patient's knee geometry, and also maintain a desired balance between the extension and flexion gap throughout the range of motion. An additional benefit of such a prosthesis may be that the components could be assembled in the joint space. This modularity of the prosthesis of the present invention may also allow the physician to implant a more standard first component while providing flexibility in the selection of a corresponding second component that may be best suited for each individual patient.

The prosthesis 10 according to the present invention may comprise a relatively hard, relatively high modulus, low friction material. Suitable materials include, for example, metals such as steel or titanium, metal alloys, ceramics, and reinforced and non-reinforced thermoset or thermoplastic polymers. The material of construction may be chosen such that the top face spans defects in the femur without deforming into the defects, allowing for the provision of recessed or non-contacting areas of the prosthesis to encourage articular regeneration. In the case of a modular prosthesis, the components need not be formed of the same material. For example, a first component may be relatively hard, whereas a conformal second component may be constructed from a relatively lower modulus material to allow for some deformation. Furthermore, the prosthesis 10 need not be made only of a single material. Rather, the prosthesis 10 or components thereof may each have areas of lower or higher modulus material, and composite structures of steel/thermoplastic, steel/ceramic, ceramic/polymer, or others may be used.

In greater detail, materials of construction could include, but are not limited to, elastomeric polymers such as nylon, silicone, polyurethane, polypropylene, polyester, or the like, optionally fiber-reinforced, or viscous-elastic materials such as PVA hydrogels, as well as other hydrophilic materials or hydrophobic materials. Polymers capable of containing living cells could also be utilized. Still other possible materials are those which can replicate the function of naturally occurring cartilage or meniscus. A surface coating can be employed, such as for the reduction of friction between the prosthesis and the femoral condyle. Generally, the areas of the prosthesis 10 expected to have the most wear may be made of stronger, more abrasion resistant material than the remainder of the prosthesis when composite structures are used. As such, it is understood that particular areas may be softer than the material used for constructing the majority of the prosthesis 10.

In accordance with the present invention, the prosthesis 10 may be manufactured so as to substantially contain, or have deposited thereon, a biologically or pharmaceutically active material such as, for example, one that promotes tissue regrowth, retards tissue degeneration, or decreases inflammation. This may be particularly suitable when the prosthesis functions to bridge a defective area of bone or articular cartilage. The active material may be provided in the form of a coating anywhere on the prosthesis 10, or may be contained within the prosthesis in the form of a solid, liquid, gel, paste, or soft polymer material. Such active materials may be designed to be delivered at once or in a timed-release manner.

It is known that the erosion of articular cartilage that occurs in an osteoarthritic patient exposes the subchondral bone, often known as eburnation. Nociceptor endings of small diameter axons (nerve endings) that are present in the bone via the bone marrow are now subject to activation by biomechanical forces associated with weight bearing. Further, higher than normal intraosseous pressure (fluid pressure present in the cancellous (trabecular) and highly mineralized (subchondral) bone) are known to exist in a large percentage of OA patients. The combination of these events is considered a likely source of a large amount of the pain felt by a patient with OA.

Biomechanical forces causing pain would likely occur during activity. In a procedure known as percutaneous vertebroplasty, bone cement, usually PMMA, is injected into the cavitated vertebral body that has partially or is at risk of collapsing. The injected cement hardens and increases the mechanical strength of the bone. As expected, bone deformation under load is decreased and reduces the mechanical forces applied to the nociceptive nerve endings and further, the PMMA is known to be toxic for nerve tissue and this procedure causes at least a partial denervation of the bone matrix, yielding immediate pain relief for the patient.

Higher than normal fluid pressure in the bone is suspected as the cause for the "bone-throbbing" pain often felt at night by these patients. Transplant patients taking cyclosporine, a known vasoconstrictor, are subject to severe, episodic knee pain in the absence of any apparent articular pathology. This phenomenon is readily controlled, however, by administration of a vasodilator, nifedipine.

According to the present invention, when the subchondral bone is perforated in preparation for the keel 22, immediate reduction of intraosseous pressure may be noted because of the obvious bleeding that occurs. If the keel 22 and perhaps the bottom face 14 are coated with a vasodilator such as nifedipine or similar acting pharmaceutical agents, one can expect continued reduction of the intraosseous pressure. Time delay of this medication may be utilized so that short term healing of the bone lesion can occur without continued bleeding and, once healed, maintain the vasodilation activity for an extended period of time.

Further, if additional nerve-targeting agents that are known to be toxic to nerve fibers (i.e., PMMA) or have the ability to desensitize the nerve endings through overstimulation (i.e., capsaicin) can also be added to the prosthesis 10, especially in that area of the prosthesis 10 with the most direct access to these fibers, such as the keel 22. These agents would be intended to disperse or leach out of the prosthesis 10 itself via a coating added to the prosthesis 10 or held in a pocketed reservoir within the prosthesis 10. Combinations of such agents would be the likely methodology, whether mixed together, applied to separate regions of the prosthesis 10, or having dual functionality.

Figure 110:
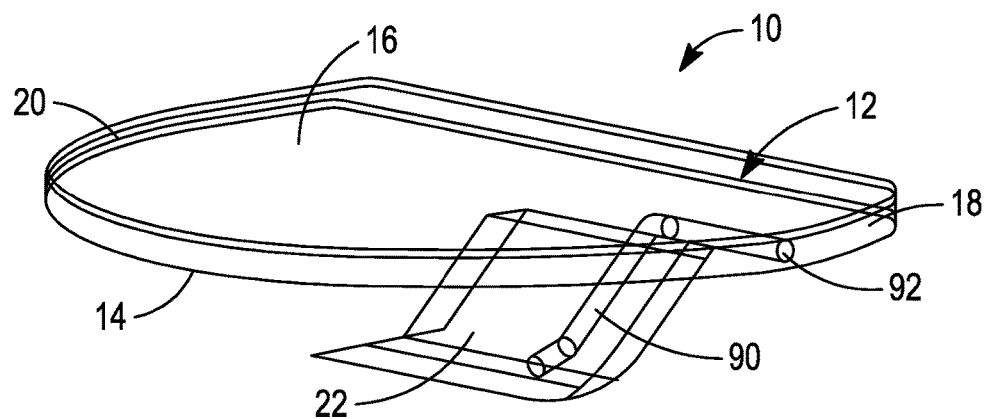
FIG. 110 is a wireframe representation of a prosthesis according to the present invention including an internal conduit and portal.

Finally, with reference to FIG. 110, the prosthesis 10, at some point after the initial implantation, having expended its reservoir of such agents, can also contain at least one internal conduit 90 that would allow for a surgeon to reapply the agents via a portal 92 that is accessible from the exposed edge of the prosthesis 10 and leads to that region of the keel 22 below the topmost surface of the subchondral bone and perhaps to the underside of the prosthesis 10 that rests on the subchondral bone. Applications of such active agents to any keeled or posted implant as used in the hip, thumb, big toe, vertebra and other joints in the body would have similar function and pain relieving purpose.

Figure 92:
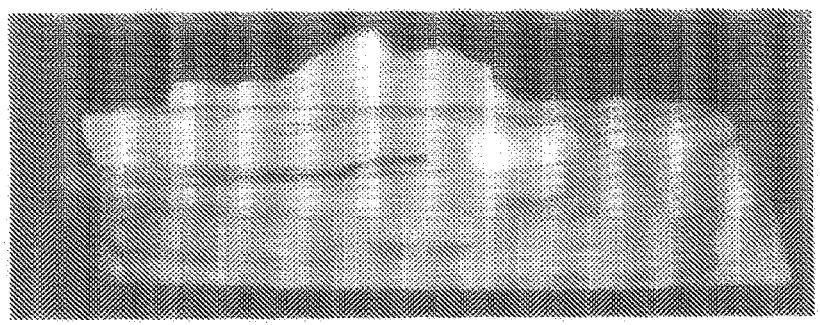
FIG. 92 is a schematic representation of a tibia, wherein the lighter volume shown in cross-section represents a typical amount of bone resection required for a prior art unicompartmental knee replacement procedure.
Figure 93:
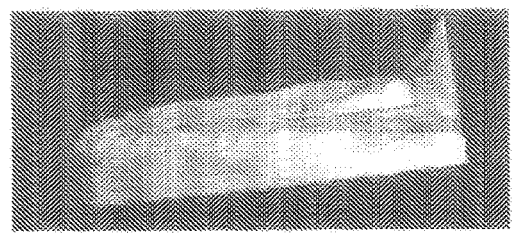
FIG. 93 is a schematic representation of a tibia, wherein the total volume represents a typical amount of bone resection required for a prior art unicompartmental knee replacement procedure, and the upper, lighter volume represents a typical amount of bone resection utilized for implanting a prosthesis according to the present invention.
Figure 94:
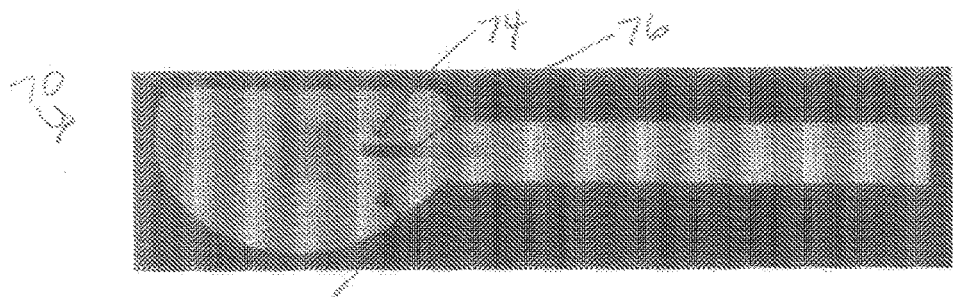
FIG. 94 is a top plan view of an instrument according to the present invention which may be utilized for creating a tibial cut in order to implant a prosthesis according to the present invention.
Figure 95:
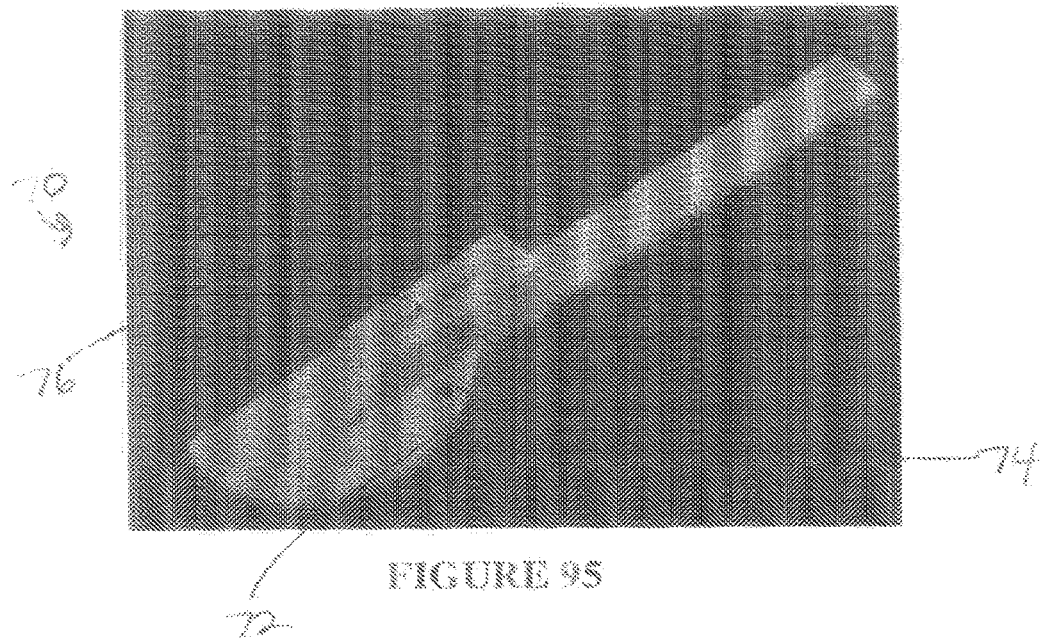
FIG. 95 is a top perspective view of the instrument of FIG. 94.
Figure 96:
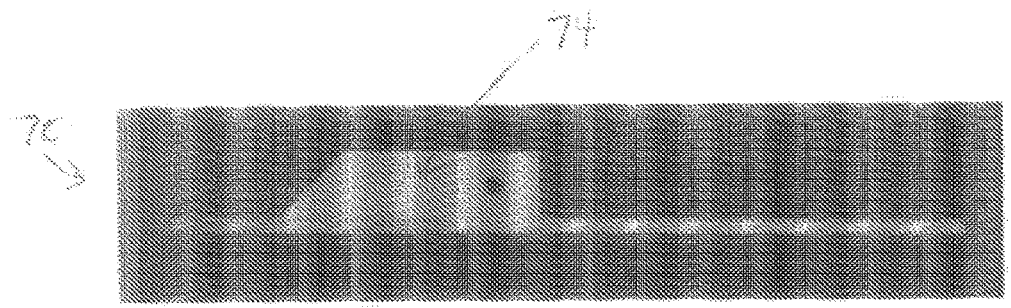
FIG. 96 is a side elevational view of the instrument of FIG. 94.
Figure 97:
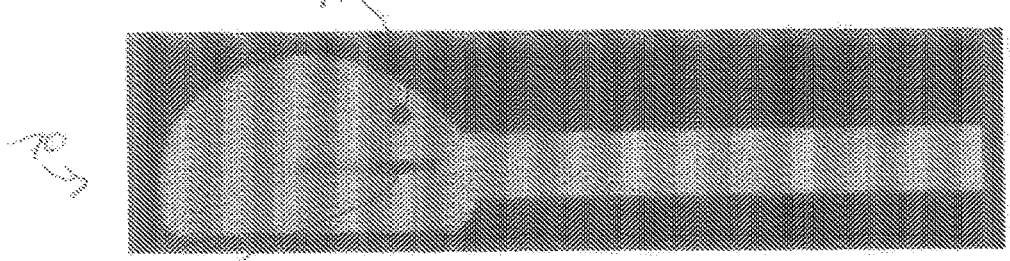
FIG. 97 is a bottom plan view of the instrument of FIG. 94.
Figure 98:
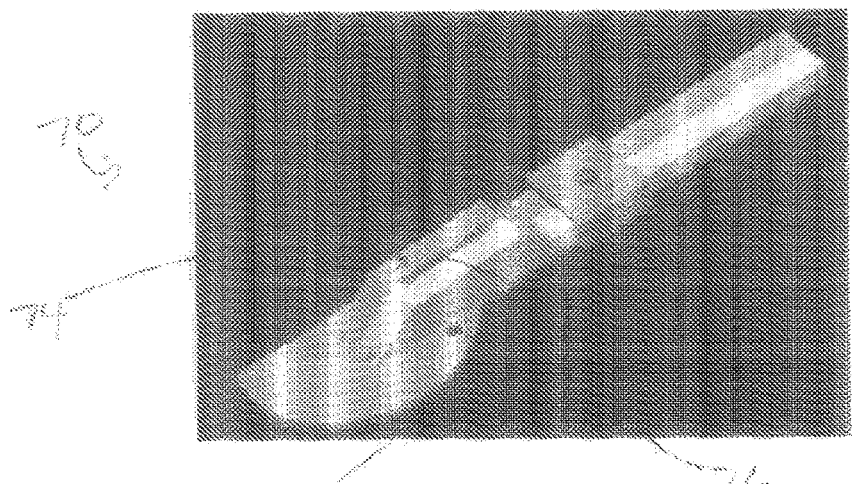
FIG. 98 is a top perspective view of a modular instrument according to the present invention which may be utilized for creating a tibial cut in order to implant a prosthesis according to the present invention.

Turning now to FIG. 92, a schematic representation of a tibia T is depicted wherein the lighter volume shown in cross-section represents a typical amount of bone resection required for a prior art unicompartmental knee replacement procedure. FIG. 93 is a schematic representation of a tibia T, wherein the total volume represents a typical amount of bone resection required for a prior art unicompartmental knee replacement procedure, and the upper volume shown in white represents the lesser amount of bone resection utilized for implanting a prosthesis 10 according to the present invention.

Figure 99:
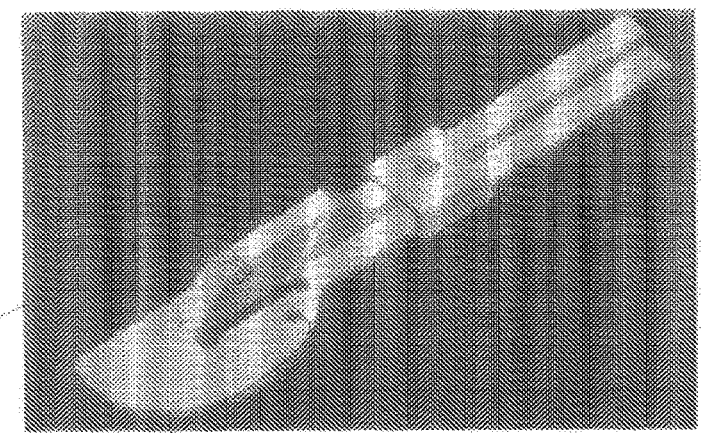
FIG. 99 is a top perspective view of the instrument of FIG. 98 where one portion of the tibial cut guide has been removed.
Figure 100:
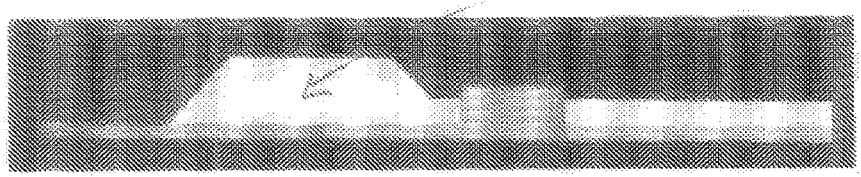
FIG. 100 is a side elevational view of the instrument of FIG. 98.
Figure 101:
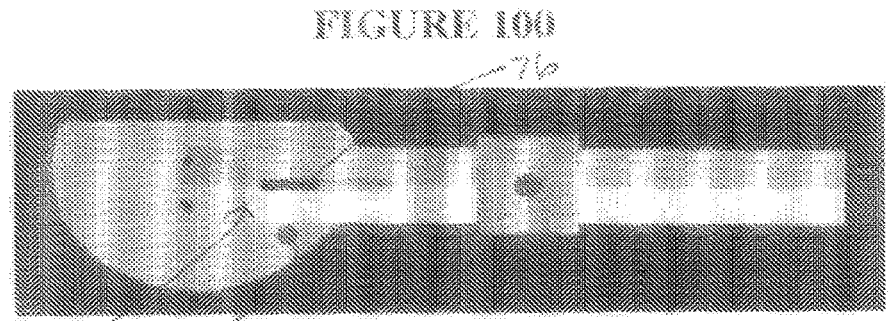
FIG. 101 is a top plan view of the instrument of FIG. 98.
Figure 102:
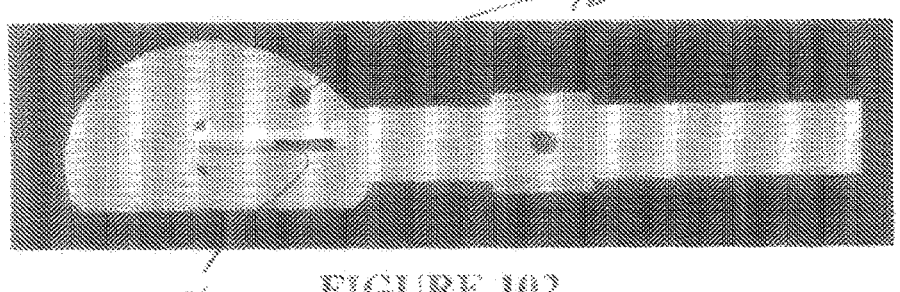
FIG. 102 is a bottom plan view of the instrument of FIG. 98.
Figure 103:
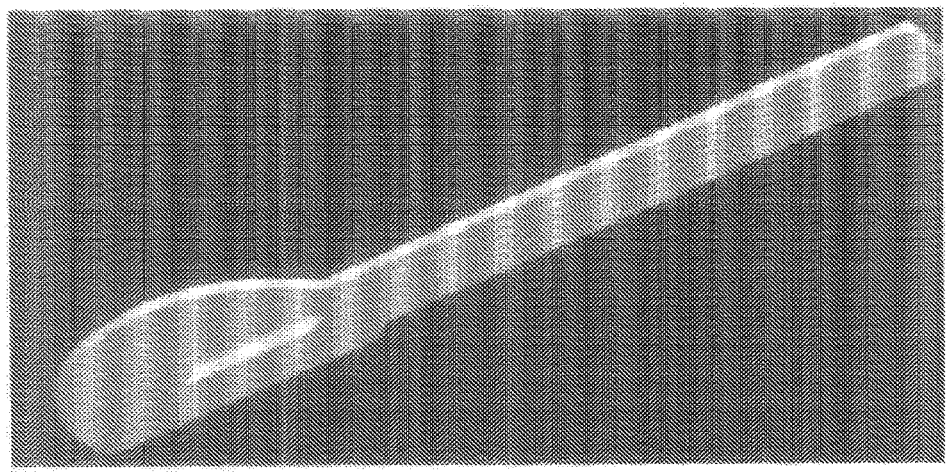
FIG. 103 is a bottom perspective view of an instrument according to the present invention for sizing a prosthesis.
Figure 104:
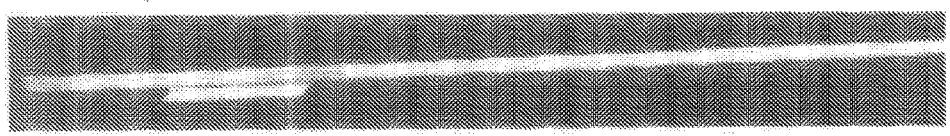
FIG. 104 is a side elevational view of the instrument of FIG. 103.
Figure 105:
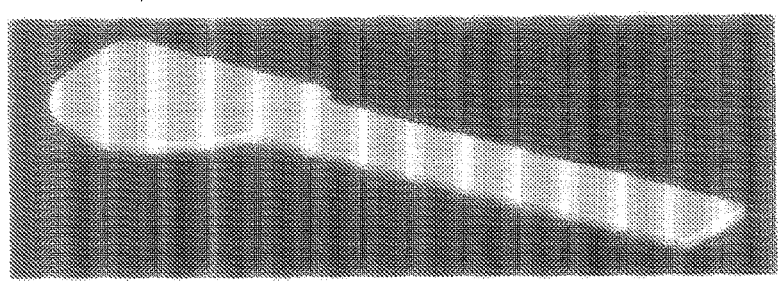
FIG. 105 is a top perspective view of the instrument of FIG. 103.
Figure 106:
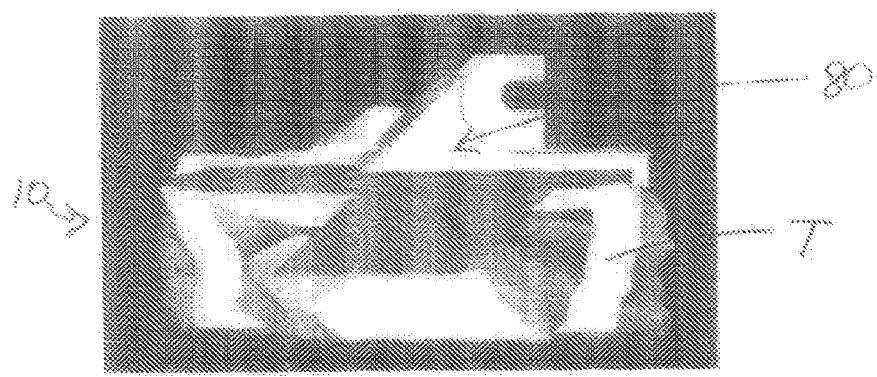
FIG. 106 is a side elevational view of an impactor according to the present invention in contact with a prosthesis according to the present invention shown with reference to a cross-section of a tibia, wherein a representative thickness subchondral and cortical bone are represented.
Figure 107:
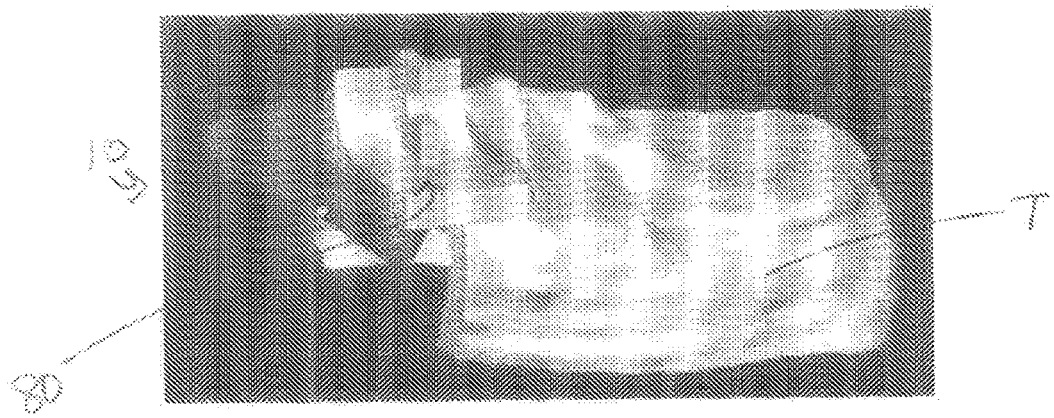
FIG. 107 is a top perspective view of the impactor of FIG. 106.
Figure 108:
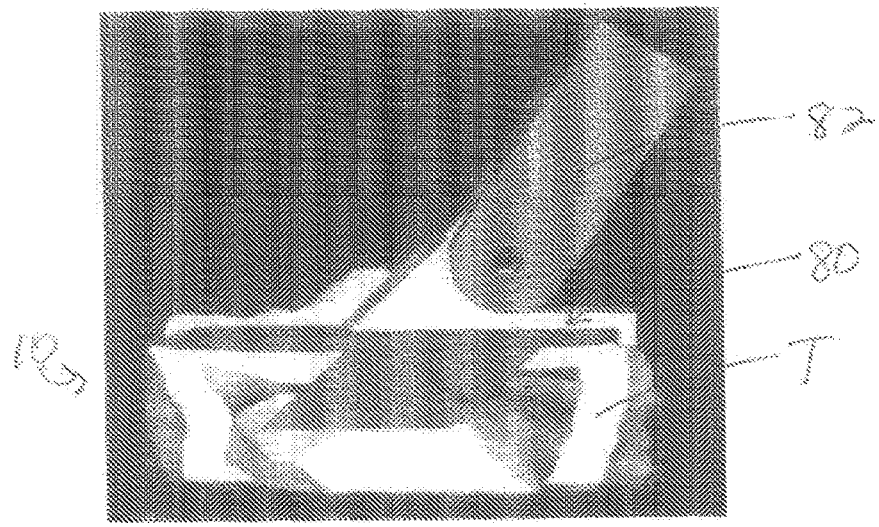
FIG. 108 is a side elevational view of the impactor of FIG. 106 further illustrating a handle thereon.
Figure 109:
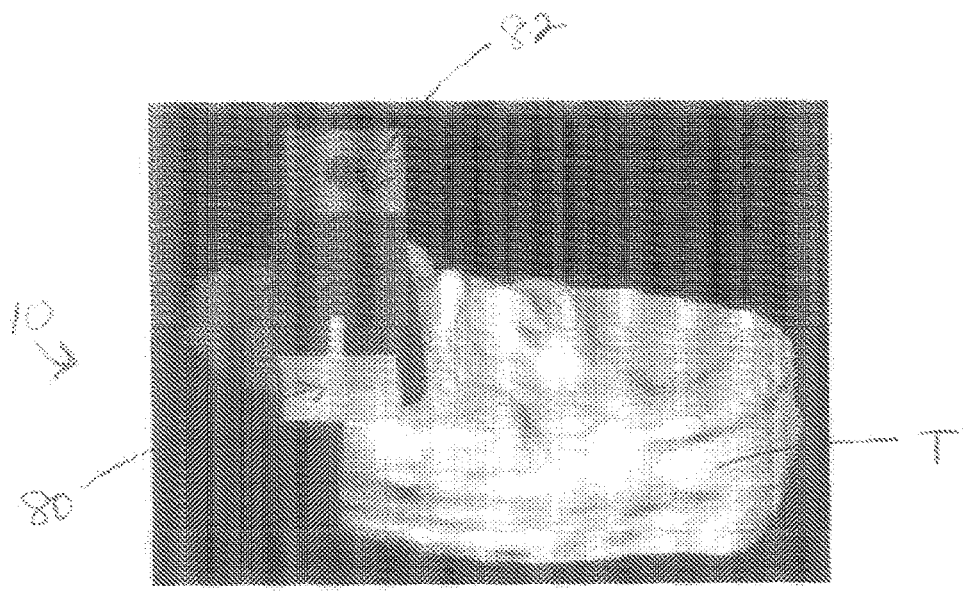
FIG. 109 is a top perspective view of the impactor and handle of FIG. 108.

FIGS. 94-97 depict an instrument 70 according to the present invention which may be utilized for creating a tibial cut in order to implant a prosthesis 10 according to the present invention. The instrument 70 shown may be placed on top of the flattened tibial plateau and may be pinned or otherwise secured in place, such as using the illustrated hole 72. The instrument 70 also includes a tibial cut guide 74 having a slot 76 which may be formed at an angle that corresponds to the angle of the keel of the prosthesis to be implanted. FIGS. 98-102 illustrate a modular instrument 70 according to the present invention which may be utilized for creating a tibial cut in order to implant a prosthesis according to the present invention. In particular, FIG. 99 is a top perspective view of the instrument of FIG. 98 where one portion of the tibial cut guide 74 has been removed. The modular instrument 70 may then be assembled with different guide components for generating cuts for different sizes and locations of a keel to be inserted. FIGS. 103-105 depict an instrument 78 according to the present invention for sizing a tibial cut, so as to ensure that the cut has been made correctly for the prosthesis to be implanted. Lastly, FIGS. 106-109 depict an impactor 80 according to the present invention in contact with a prosthesis 10 according to the present invention shown with reference to a cross-section of a tibia T. In accordance with one aspect of the present invention, the impactor 80 may be configured to engage the prosthesis 10 toward the middle thereof, and the handle 82 may have the ability to pivot as the prosthesis 10 is being inserted.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A unicompartmental knee prosthesis for implantation in a knee joint between a femoral condyle and a corresponding tibial plateau, the prosthesis comprising:
    a generally elliptical baseplate having opposed femoral and tibial faces, the baseplate having an anterior end and a posterior end; and
    a keel connected to the tibial face in an anterior-posterior orientation relative to the baseplate, wherein the keel has a first continuous taper from a proximal end of the keel at the connection to the tibial face to a distal end of the keel such that the proximal end is wider than the distal end, and wherein the keel has a second continuous taper from a keel anterior end to a keel posterior end such that the keel anterior end is wider than the keel posterior end.

2. The prosthesis of claim 1, wherein the keel has a distal posterior portion that extends farther toward the posterior end of the baseplate as compared with a proximal posterior portion of the keel.

3. The prosthesis of claim 2, wherein the distal posterior portion is hook-shaped to form an obtuse angle at the keel posterior end.

4. The prosthesis of claim 1, wherein the keel posterior end at the distal end is disposed closer to the tibial face than the keel anterior end at the distal end.

5. The prosthesis of claim 1, wherein the keel anterior end is relatively longer in a proximal-distal direction than the keel posterior end and the keel anterior end is angled relative to the tibial face such that the keel anterior end at the distal end is disposed further away from a distal end of the baseplate than the keel anterior end at a proximal end of the baseplate.

6. The prosthesis of claim 1, wherein the distal end of the keel is configured as a knife edge.

7. The prosthesis of claim 1, wherein the keel is constructed from a deformable material.

8. The prosthesis of claim 1, wherein the keel has a depth proximal-distal from the tibial face of 2 to 3 mm.

9. The prosthesis of claim 1, the baseplate and keel are formed as a monolithic component.

10. The prosthesis of claim 1, wherein the prosthesis includes a biologically or pharmaceutically active material associated therewith.

11. The prosthesis according to claim 10, wherein the biologically or pharmaceutically active material is a vasodilator associated with the keel.

12. The prosthesis according to claim 11, wherein the biologically or pharmaceutically active material is a nerve-targeting agent associated with the keel.

13. A unicompartmental knee prosthesis for implantation in a knee joint between a femoral condyle and a corresponding tibial plateau, the prosthesis comprising:
    a generally elliptical baseplate having opposed femoral and tibial faces, the baseplate having an anterior end and a posterior end; and
    a keel connected to the tibial face in an anterior-posterior orientation relative to the baseplate, the keel tapers such that a proximal end of the keel adjacent the tibial face is wider than a distal end of the keel, wherein the keel tapers such that a keel anterior end is wider than a keel posterior end, and wherein the keel anterior end is relatively longer in a proximal-distal direction than the keel posterior end and the anterior end is angled relative to the tibial face such that the keel anterior end at the distal end is disposed further away from a distal end of the baseplate than the keel anterior end at a proximal end of the baseplate.

14. The prosthesis of claim 13, wherein the keel has a distal posterior portion that extends farther toward the posterior end of the baseplate as compared with a proximal posterior portion of the keel.

15. The prosthesis of claim 14, wherein the distal posterior portion is hook-shaped to form an obtuse angle at the keel posterior end.

16. The prosthesis of claim 13, wherein the distal end of the keel is configured as a knife edge.

17. A unicompartmental knee prosthesis for implantation in a knee joint between a femoral condyle and a corresponding tibial plateau, the prosthesis comprising:
    a generally elliptical baseplate having opposed femoral and tibial faces, the baseplate having an anterior end and a posterior end; and
    a keel connected to the tibial face in an anterior-posterior orientation relative to the baseplate, the keel has a first continuous taper from a proximal end of the keel at the connection to the tibial face to a distal end of the keel such that the proximal end is wider than the distal end of the keel, wherein the keel has a second continuous taper from a keel anterior end to a keel posterior end such that the keel anterior end is wider than the keel posterior end, and wherein the keel has a distal posterior portion that extends farther toward the posterior end of the baseplate as compared with a proximal posterior portion of the keel.

18. The prosthesis of claim 17, wherein the keel anterior end is relatively longer in a proximal-distal direction than the keel posterior end and the anterior end is angled relative to the tibial face such that the keel anterior end at the distal end is disposed further away from the distal end of the baseplate than the keel anterior end at the proximal end.

19. The prosthesis of claim 17, wherein the distal posterior portion is hook-shaped to form an obtuse angle at the keel posterior end.

\* \* \* \* \*